US006277885B1

(12) United States Patent
Levin et al.

(10) Patent No.: US 6,277,885 B1
(45) Date of Patent: Aug. 21, 2001

(54) ACETYLENIC ARYL SULFONAMIDE AND PHOSPHINIC ACID AMIDE HYDROXAMIC ACID TACE INHIBITORS

(75) Inventors: Jeremy I. Levin, New City, NY (US); James M. Chen, Stoddard Court, NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/491,636

(22) Filed: Jan. 27, 2000

Related U.S. Application Data
(60) Provisional application No. 60/155,204, filed on Jan. 27, 1999.

(51) Int. Cl.[7] .................. A61K 31/185; C07C 259/08
(52) U.S. Cl. .................. 514/575; 514/521; 514/118; 514/112; 558/386; 558/390; 558/397; 562/622
(58) Field of Search .................. 562/622; 558/386, 558/390, 397; 514/575, 521, 118

(56) References Cited

U.S. PATENT DOCUMENTS

| | | | |
|---|---|---|---|
| 5,455,258 | 10/1995 | MacPherson et al. | 514/357 |
| 5,506,242 | 4/1996 | MacPherson et al. | 514/336 |
| 5,552,419 | 9/1996 | MacPherson et al. | 514/357 |
| 5,753,653 | 5/1998 | Bender et al. | 514/227.5 |
| 5,770,624 | 6/1998 | Parker | 514/575 |
| 5,804,593 | 9/1998 | Warpechoski et al. | 514/419 |
| 5,817,822 | 10/1998 | Nantermet et al. | 546/194 |
| 5,929,097 | 7/1999 | Levin et al. | 514/351 |

FOREIGN PATENT DOCUMENTS

| | | |
|---|---|---|
| 19542189 | 5/1997 | (DE) . |
| 606046 | 12/1993 | (EP) . |
| 757037 | 7/1996 | (EP) . |
| 757984 | 8/1996 | (EP) . |
| 803505 | 4/1997 | (EP) . |
| WO9535275 | 12/1995 | (WO) . |
| WO9535276 | 12/1995 | (WO) . |
| WO9600214 | 1/1996 | (WO) . |
| WO9627583 | 9/1996 | (WO) . |
| WO9633172 | 10/1996 | (WO) . |
| WO9718194 | 5/1997 | (WO) . |
| WO9719068 | 5/1997 | (WO) . |
| WO9720824 | 6/1997 | (WO) . |
| WO9722587 | 6/1997 | (WO) . |
| WO9727174 | 7/1997 | (WO) . |
| WO9745402 | 12/1997 | (WO) . |
| WO9803166 | 1/1998 | (WO) . |
| WO9807697 | 2/1998 | (WO) . |
| WO9808815 | 3/1998 | (WO) . |
| WO9808822 | 3/1998 | (WO) . |
| WO9808823 | 3/1998 | (WO) . |
| WO9808825 | 3/1998 | (WO) . |
| WO9808827 | 3/1998 | (WO) . |
| WO9808853 | 3/1998 | (WO) . |
| WO9816503 | 4/1998 | (WO) . |
| WO9816506 | 4/1998 | (WO) . |
| WO9816514 | 4/1998 | (WO) . |
| WO9816520 | 4/1998 | (WO) . |
| WO9827069 | 6/1998 | (WO) . |
| WO9831664 | 7/1998 | (WO) . |
| WO9833768 | 8/1998 | (WO) . |
| WO9834918 | 8/1998 | (WO) . |
| WO9839313 | 9/1998 | (WO) . |
| WO9839329 | 9/1998 | (WO) . |
| WO9842659 | 10/1998 | (WO) . |
| WO9843963 | 10/1998 | (WO) . |

OTHER PUBLICATIONS

Shire, M.G., Exp. Opin. Ther. Patents 8(5), 531 (1998).
Grossman, J.M., Woman's Health, 6(6), 627 (1997).
Isomaki, P.J., Ann. Med., 29, 499 (1997).
Camussi, G., Drugs, 55(5), 613 (1998).
Mathison et al., J. Clin Invest., 81 1925, (1988).
Miethke et al., J. Exp. Med., 175, 91 (1992).
Piquet, P. F., J. Exp. Med. 166, 1280 (1987).
Beuther, B., Ann. Rev., Biochem, 57, 505 (1988).
Ksontini, R., Arch, Surg., 133, 558, (1998).
Packer, M., Circulation, 92(6), 1379 (1995).
Ferrari, R., et al., Circulation 92(6), 1479 (1995).
Hotamisligil, G.S. et al., Science, 259, 87 (1993).
Peterson, P.K. et al., J. Clin. Invest., 89, 574 (1992).
Pallares–Trujillo et al., Med. Res. Reviews, 15(6), 533 (1995).
Old, L., Science, 230, 630 (1985).
Rankin, E.C. et al., Br. J. Rheumatol., 34, 334 (1995).
Pharmaprojects, Therapeutic Updates 17 (Oct.) au 197, M2Z (1996).
McGeehan et al, Current Pharmaceutical Design, 2, 662 (1996).
Script 20, 2349 (1998).
MacPherson et al., J. Med. Chem., 40, 2525 (1997).
Tamura et al., J. Med. Chem. 41, 640 (1998).
Levin et al., Bioorg. & Med. Chem. Letters, 8, 2657 (1998).
Pikul et al., J. Med. Chem., 41, 3568 (1998).

Primary Examiner—Richard L. Raymond
(74) Attorney, Agent, or Firm—John W. Hogan, Jr.

(57) ABSTRACT

Hydroxamic acids having the formula

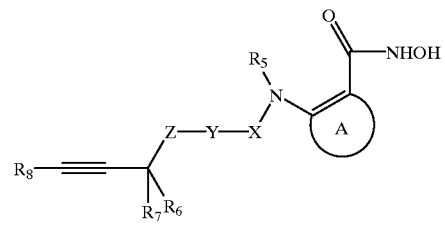

are useful in treating disease conditions mediated by TNF-α, such as rheumatoid arthritis, osteoarthritis, sepsis, AIDS, ulcerative colitis, multiple sclerosis, Crohn's disease and degenerative cartilage loss.

13 Claims, No Drawings

ACETYLENIC ARYL SULFONAMIDE AND PHOSPHINIC ACID AMIDE HYDROXAMIC ACID TACE INHIBITORS

This application claims the benefit of U.S. Provisional Application No. 60/155,204, filed Jan. 27, 1999.

FIELD OF INVENTION

This invention relates to acetylenic aryl sulfonamide hydroxamic acids which act as inhibitors of TNF-α converting enzyme (TACE). The compounds of the present invention are useful in disease conditions mediated by TNF-α, such as rheumatoid arthritis, osteoarthritis, sepsis, AIDS, ulcerative colitis, multiple sclerosis, Crohn's disease and degenerative cartilage loss.

BACKGROUND OF THE INVENTION

TNF-α converting enzyme (TACE) catalyzes the formation of TNF-α from membrane bound TNF-α precursor protein. TNF-α is a pro-inflammatory cytokine that is believed to have a role in rheumatoid arthritis [Shire, M. G.; Muller, G. W. *Exp. Opin. Ther. Patents* 1998, 8(5), 531; Grossman, J. M.; Brahn, E. J. *Women's Health* 1997, 6(6), 627; Isomaki, P.; Punnonen, J. *Ann. Med.* 1997, 29, 499; Camussi, G.; Lupia, E. *Drugs*, 1998, 55(5), 613.] septic shock [Mathison, et. al. *J. Clin. Invest.* 1988, 81, 1925; Miethke, et. al. *J. Exp. Med.* 1992, 175, 91.], graft rejection [Piguet, P. F.; Grau, G. E.; et. al. *J. Exp. Med.* 1987, 166, 1280.], cachexia [Beutler, B.; Cerami, A. *Ann. Rev. Biochem.* 1988, 57, 505.], anorexia, inflammation [Ksontini, R,; MacKay, S. L. D.; Moldawer, L. L. *Arch. Surg.* 1998, 133, 558.], congestive heart failure [Packer, M. *Circulation*, 1995, 92(6), 1379; Ferrari, R.; Bachetti, T.; et. al. *Circulation*, 1995, 92(6), 1479.], post-ischaemic reperfusion injury, inflammatory disease of the central nervous system, inflammatory bowel disease, insulin resistance [Hotamisligil, G. S.; Shargill, N. S.; Spiegelman, B. M.; et. al. *Science*, 1993, 259, 87.] and HIV infection [Peterson, P. K.; Gekker, G.; et. al. *J. Clin. Invest.* 1992, 89, 574; Pallares-Trujillo, J.; Lopez-Soriano, F. J. Argiles, J. M. *Med. Res. Reviews*, 1995, 15(6), 533.]], in addition to its well-documented antitumor properties [Old, L. *Science*, 1985, 230, 630.]. For example, research with anti-TNF-α antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A.; Panayi, G. S. *Br. J. Rheumatol.* 1995, 34, 334; *Pharmaprojects*, 1996, Therapeutic Updates 17 (Oct.), aul97-M2Z.]. This observation has recently been extended to humans as well as described in "TNF-α in Human Diseases", *Current Pharmaceutical Design*, 1996, 2, 662.

It is expected that small molecule inhibitors of TACE would have the potential for treating a variety of disease states. Although a variety of TACE inhibitors are known, many of these molecules are peptidic and peptide-like which suffer from bioavailability and pharmacokinetic problems. In addition, many of these molecules are non-selective, being potent inhibitors of matrix metalloproteinases and, in particular, MMP-1. Inhibition of MMP-1 (collagenase 1) has been postulated to cause joint pain in clinical trials of MMP inhibitors [Scrip, 1998, 2349, 20] Long acting, selective, orally bioavailable non-peptide inhibitors of TACE would thus be highly desirable for the treatment of the disease states discussed above.

Examples of sulfonamide hydroxamic acid MMP/TACE inhibitors in which a 2 carbon chain separates the hydroxamic acid and the sulfonamide nitrogen, as shown below, are disclosed in WIPO international publications WO9816503, WO9816506, WO9816514 and WO9816520 and U.S. Pat. No. 5,776,961.

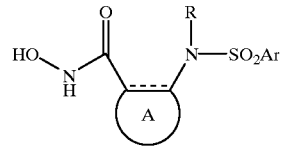

U.S. Pat. Nos. 5,455,258, 5,506,242, 5,552,419, 5,770,624, 5,804,593 and 5,817,822 as well as European patent application EP606,046A1 and WIPO international publications WO9600214 and WO9722587 disclose non-peptide inhibitors of matrix metalloproteinases and/or TACE of which the aryl sulfonamide hydroxamic acid shown below, in which 1 carbon separates the hydroxarnic acid and the sulfonamide nitrogen, is representative. Additional publications disclosing sulfonamide based MMP inhibitors which are variants of the sulfonamidehydroxamate shown below, or the analogous sulfonamide-carboxylates, are European patent applications EP-757037-A1 and EP-757984-A1 and WIPO international publications WO9535275, WO9535276, WO9627583, WO9719068, WO9727174, WO9745402, WO9807697, and WO9831664, WO9833768, WO9839313, WO9839329, WO9842659 and WO9843963. The discovery of this type of MMP inhibitor is further detailed by MacPherson, et. al. in *J. Med. Chem.*, (1997), 40, 2525 and Tamura, et. al. in *J. Med. Chem.* (1998), 41, 640.

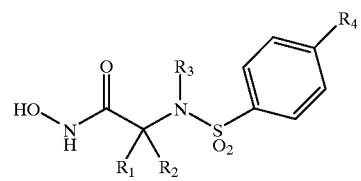

Publications disclosing β-sulfonamide-hydroxamate inhibitors of MMPs and/or TACE in which the carbon alpha to the hydroxamic acid has been joined in a ring to the sulfonamide nitrogen, as shown below, include U.S. Pat. No. 5,753,653, WIPO international publications WO9633172, WO9720824, WO9827069, WO9808815, WO9808822, WO9808823, WO9808825, WO9834918, WO9808827, Levin, et. al. *Bioorg. & Med. Chem. Letters* 1998, 8, 2657 and Pikul, et. al. *J. Med. Chem.* 1998, 41, 3568.

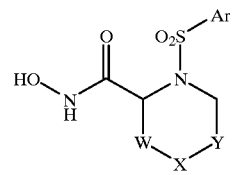

The patent applications DE19,542,189-A1, WO9718194, and EP803505 disclose additional examples of cylic sulfonamides as MMP and/or TACE inhibitors. In this case the sulfonamide-containing ring is fused to a aromatic or heteroaromatic ring.

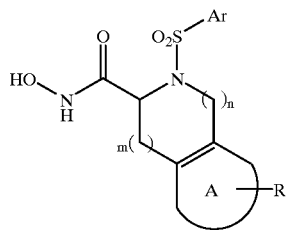

Analogous to the sulfonamides are the phosphinic acid amide hydroxamic acid MMP/TACE inhibitors, exemplified by the structure below, which have been disclosed in WIPO international publication WO9808853.

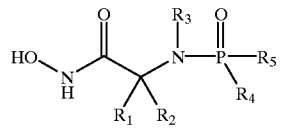

Sulfonamide MMP/TACE inhibitors in which a thiol is the zinc chelating group, as shown below, have been disclosed in WIPO international application 9803166.

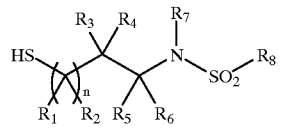

It is an object of this invention to disclose aryl sulfonamide hydroxamic acid MMP/TACE inhibitors in which the sulfonyl aryl group is para-substituted with a substituted butynyl moiety or a propargylic ether, amine or sulfide. These compounds provide enhanced levels of inhibition of the activity of TACE in vitro and in a cellular assay and/or selectivty over MMP-1. These compounds may therefore be used in the treatment of diseases mediated by TNF.

DETAILED DESCRIPTION OF THE INVENTION

The TACE and MMP inhibiting ortho-sulfonamido aryl hydroxamic acids of the present invention are represented by the formula:

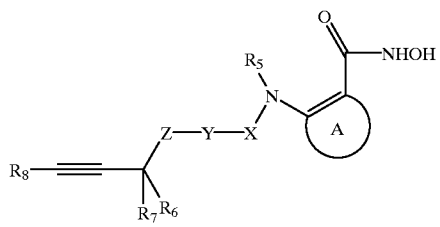

where the C(=O)NHOH moiety and the —NR$^5$—moiety are bonded to adjacent carbons of group A;

Wherein A is phenyl, naphthyl, or phenyl fused to a 5 to 7 membered saturated or unsaturated cycloalkyl ring, a 5 to 9 membered saturated or unsaturated heterocycloalkyl ring having 1 or 2 heteroatoms selected from N, NR9, O or S, or a heteroaryl ring having 5–10 members and from 1–3 heteroatoms selected from N, NR9, O or S;

X is SO$_2$ or —P(O)R$_{10}$;

Y is phenyl, naphthyl or 5–10 membered heteroaryl having from 1 to 3 heteroatoms selected from N, NR$_9$, O or S; with the proviso that X and Z may not be bonded to adjacent atoms of Y;

Z is O, NH, CH$_2$, or S;

R$_5$ is hydrogen or alkyl of 1–6 carbon atoms;

or R$_5$—N—A—, can form a benzazepine, benzoxazepine, benzothiazepine, benzodiazepine, benzazocine, benzodiazocine, benzoxazocine or benzothiazocane ring which may be optionally fused to another benzene ring;

R$_6$ and R$_7$ are each, independently, hydrogen, alkyl of 1–6 carbon atoms, —CN, —CCH;

and R$_8$ is hydrogen, alkyl of 1–6 carbon atoms, alkenyl of 2–6 carbon atoms, alkynyl of 2–6 carbon atoms, cycloalkyl of 3–6 carbon atoms, phenyl, naphthyl, 5 to 10 membered heteroaryl having from 1 to 3 heteoatoms selected from N, NR9, O or S, or 5 to 9 membered heterocycloalkyl having 1 or 2 heteroatoms selected from N, NR9, O or S;

R$_9$ is hydrogen, phenyl, naphthyl, alkyl of 1–6 carbon atoms, or cycloalkyl of 3–6 carbon atoms;

and R$_{10}$ is phenyl, naphthyl, alkyl of 1–6 carbon atoms, cycloalkyl of 3–6 carbon atoms, 5 to 10 membered heteroaryl having from 1 to 3 heteoatoms selected from N, NR9, O or S, or 5 to 9 membered heterocycloalkyl having 1 or 2 heteroatoms selected from N, NR9, O or S;

or a pharmaceutically acceptable salt thereof.

Preferred compounds of this invention include compounds of structure B wherein both of the carbons of A adjacent to the —NR$^5$— group has a substituent other than hydrogen.

More preferred compounds of this invention include compounds of structure B in which A is a phenyl wherein both of the carbons of A adjacent to the —NR$^5$— group has a substituent other than hydrogen, and the carbon of group A para to the —NR$^5$— group has a substituent other than hydrogen.

More preferred compounds of this invention include compounds of structure B in which A is a phenyl wherein:
both of the carbons of A adjacent to the —NR$^5$— group has a substituent other than hydrogen;
the carbon of group A para to the —NR$^5$— group has a substituent other than hydrogen; and
Y is a phenyl ring substituted at the 1- and 4-positions by X and Z, respectively.

More preferred compounds of this invention include compounds of structure B in which A is a phenyl wherein:
both of the carbons of A adjacent to the —NR$^5$— group has a substituent other than hydrogen;
the carbon of group A para to the —NR$^5$— group has a substituent other than hydrogen; and
Y is a phenyl ring substituted at the 1- and 4-positions by X and Z, respectively;
and X is SO$_2$.

More preferred compounds of this invention include compounds of structure B in which A is a phenyl wherein:
both of the carbons of A adjacent to the —NR$^5$— group has a substituent other than hydrogen; and
the carbon of group A para to the —NR$^5$— group has a substituent other than hydrogen;

Y is a phenyl ring substituted at the 1- and 4-positions by X and Z, respectively;

X is $SO_2$;

and Z is oxygen.

More preferred compounds of this invention include compounds of structure B in which A is a phenyl wherein:

both of the carbons of A adjacent to the —$NR^5$— group has a substituent other than hydrogen; and the carbon of group A para to the —$NR^5$— group has a substituent other than hydrogen;

Y is a phenyl ring substituted at the 1- and 4-positions by X and Z, respectively;

X is $SO_2$;

Z is oxygen;

and $R_6$ and $R_7$ are hydrogen.

More preferred compounds of this invention include compounds of structure B in which A is a phenyl wherein:

both of the carbons of A adjacent to the —$NR^5$— group has a substituent other than hydrogen;

the carbon of group A para to the —$NR^5$— group has a substituent other than hydrogen;

Y is a phenyl ring substituted at the 1- and 4-positions by X and Z, respectively;

X is $SO_2$;

Z is oxygen;

$R_6$ and $R_7$ are hydrogen;

and $R_8$ is —$CH_2OH$ or methyl.

Most preferred compounds of the present invention include

5-Bromo-2-{[4-(4-cyclobutylamino-but-2-ynyloxy)-benzenesulfonyl]-methyl-amino}-N-hydroxy-3-methyl-benzamide;

5-Bromo-N-hydroxy-3-methyl-2-{methyl-[4-(4-methylamino-but-2-ynyloxy)-benzenesulfonyl]-amino}-benzamide;

5-Bromo-2-({4-[4-(3-dimethylamino-propylamino)-but-2-ynyloxy]-benzenesulfonyl}-methyl-amino)-N-hydroxy-3-methyl-benzamide;

5-Bromo-2-({4-[4-(2-dimethylamino-ethylamino)-but-2-ynyloxy]-benzenesulfonyl}-methyl-amino)-N-hydroxy-3-methyl-benzamide;

4-[(4-But-2-ynyloxy-benzenesulfonyl)-methyl-amino]-5-methyl-bipheny-3-carboxylic acid hydroxyamide;

5-Bromo-N-hydroxy-3-methyl-2-[methyl-(4-prop-2-ynyloxy-benzenesulfonyl)-amino]-benzamide;

5-Bromo-N-hydroxy-3-methyl-2-[methyl-(4-pent-2-ynyloxy-benzenesulfonyl)-amino]-benzamide;

5-Bromo-2-[(4-hept-2-ynyloxy-benzenesulfonyl)-methyl-amino]-N-hydroxy-3-methyl-benzamide;

5-Bromo-2-[(4-hex-2-ynyloxy-benzenesulfonyl)-methyl-amino]-N-hydroxy-3-methyl-benzamide;

5-Bromo-N-hydroxy-2-{[4-(4-methoxy-but-2-ynyloxy)-benzenesulfonyl]-methyl-amino}-3-methyl-benzamide;

5-Bromo-N-hydroxy-3-methyl-2-{methyl-[4-(3-phenyl-prop-2-ynyloxy)-benzenesulfonyl]-amino}-benzamide;

5-Bromo-N-hydroxy-2-({4-[3-(3-methoxy-phenyl)-prop-2-ynyloxy]-benzenesulfonyl}-methyl-amino)-3-methyl-benzamide;

5-Bromo-N-hydroxy-2-({4-[3-(2-methoxy-phenyl)-prop-2-ynyloxy]-benzenesulfonyl}-methyl-amino)-3-methyl-benzamide;

5-Bromo-N-hydroxy-2-({4-[3-(4-methoxy-phenyl)-prop-2-ynyloxy]-benzenesulfonyl}-methyl-amino)-3-methyl-benzamide;

2-[(4-But-2-ynyloxy-benzenesulfonyl)-methyl-amino]-N-hydroxy-5-iodo-3-methyl-benzamide;

2-[Benzyl-(4-but-2-ynyloxy-benzenesulfonyl)-amino]-N-hydroxy-3,5-dimethyl-benzamide;

5-Bromo-N-hydroxy-3-methyl-2-{methyl-[4-(4-pyrrolidin-1-yl-but-2-ynyloxy)-benzenesulfonyl]-amino}-benzamide;

5-Bromo-2-{[4-(4-diethylamino-but-2-ynyloxy)-benzenesulfonyl]-methyl-amino}-N-hydroxy-3-methyl-benzamide;

5-Bromo-2-[(4-but-2-ynyloxy-benzenesulfonyl)-(4-methyl-piperazin-1-ylmethyl)-amino]-N-hydroxy-3-methyl-benzamide;

5-Bromo-N-hydroxy-3-methyl-2-(methyl-{4-[4-(tetrahydro-pyran-2-yloxy)-but-2-ynyloxy]-benzenesulfonyl}-amino)-benzamide;

5-Bromo-N-hydroxy-2-{[4-(4-hydroxy-but-2-ynyloxy)-benzenesulfonyl]-methyl-amino}-3-methyl-benzamide;

4-[(4-But-2-ynyloxy-benzenesulfonyl)-methyl-amino]-5-(4-methyl-piperazin-1-ylmethyl)-biphenyl-3-carboxylic acid hydroxyamide dihydrochloride salt; and pharmaceutical salts thereof.

Heteroaryl, as used herein is a 5–10 membered mono- or bicyclic aromatic ring having from 1–3 heteroatoms selected from N, NR9, S and O. Heteroaryl is preferably

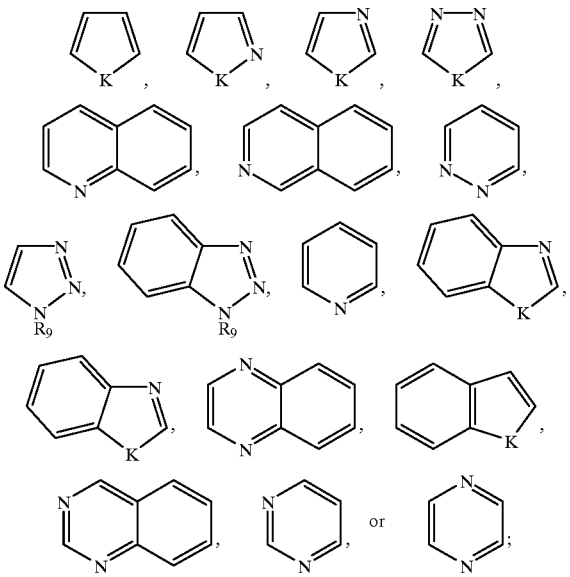

wherein K is NR9, O or S and R9 is hydrogen, phenyl, naphthyl, alkyl of 1–6 carbon atoms, or cycloalkyl of 3–6 carbon atoms. Preferred heteroaryl rings include pyrrole, furan, thiophene, pyridine, pyrimidine, pyridazine, pyrazine, triazole, pyrazole, imidazole, isothiazole, thiazole, isoxazole, oxazole, indole, isoindole, benzofuran, benzothiophene, quinoline, isoquinoline, quinoxaline, quinazoline, benzotriazole, indazole, benzimidazole, benzothiazole, benzisoxazole, and benzoxazole. Heteroaryl groups of the present invention may optionally be mono- or di-substituted.

Heterocycloalkyl as used herein refers to a 5 to 10 membered saturated or unsaturated mono or bi-cyclic ring having 1 or 2 heteroatoms selected from N, NR9, S or O. Heterocycloalkyl rings of the present invention are preferably selected from

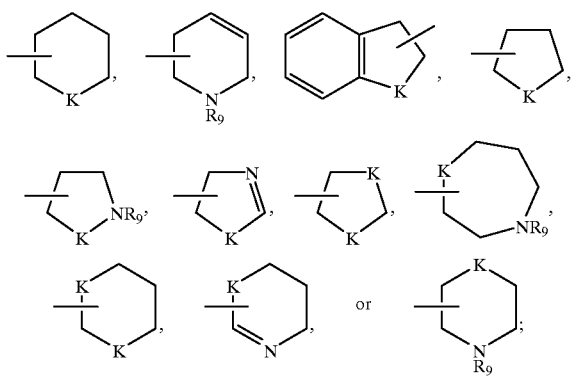

wherein K is NR9, O or S and R9 is hydrogen, phenyl, naphthyl, alkyl of 1–6 carbon atoms, or cycloalkyl of 3–6 carbon atoms. Preferred heterocycloalkyl rings include piperidine, piperazine, morpholine, tetrahydropyran, tetrahydrofuran or pyrrolidine. Heterocycloalkyl groups of the present invention may optionally be mono- or di-substituted.

Aryl, as used herein refers to phenyl or naphthyl which may, optionally be mono-, di- or tri-substituted.

Alkyl, alkenyl, alkynyl, and perfluoroalkyl include both straight chain as well as branched moieties. Alkyl, alkenyl, alkynyl, and cycloalkyl groups may be unsubstituted unsubstituted (carbons bonded to hydrogen, or other carbons in the chain or ring) or may be mono- or poly-substituted.

Halogen means bromine, chlorine, fluorine, and iodine.

Suitable substituents of aryl, heteroaryl, alkyl, alkenyl, alkynyl, cycloalkyl and include, but are not limited to halogen, alkyl of 1–6 carbon atoms, alkenyl of 2–6 carbon atoms, alkynyl of 2–6 carbon atoms, cyclocalkyl of 3–6 carbon atoms, —$OR_2$, —CN, —$COR_2$, perfluoroalkyl of 1–4 carbon atoms, —O—perfluoroalkyl of 1–4 carbon atoms, —$CONR_2R_3$, —$S(O)_nR_2$—$OPO(OR_2)OR_3$, —PO($OR_2$)$R_3$, —$OC(O)NR_2R_3$, —$C(O)NR_2OR_3$, —$COOR_2$, —$SO_3H$, —$NR_2R_3$, —$N[(CH_2)_2]_2NR_2$, —$NR_2COR_3$, —$NR_2COOR_3$, —$SO_2NR_2R_3$, —$NO_2$, —$N(R_2)SO_2R_3$, —$NR_2CONR_2R_3$, —$NR_2C(=NR_3)NR_2R_3$, —$NR_2C(=NR_3)N(SO_2)R_2R_3$, $NR_2C(=NR_3)N(C=O)R_2R_3$, $NR_2C(=NR_3)N(SO_2R_2)R_3$, $NR_2C(=NR_3)N(COR_2)R_3$, —$SO_2NHCOR_4$, —$CONHSO_2R_4$, -tetrazol-5-yl, —$SO_2NHCN$, —$SO_2NHCONR_2R_3$, phenyl, naphthyl, heteroaryl or heterocycloalkyl;

wherein —$NR_2R_3$ may form a pyrrolidine, piperidine, morpholine, thiomorpholine, oxazolidine, thiazolidine, pyrazolidine, piperazine, or azetidine ring;

$R_2$ and $R_3$ are each, independently, hydrogen, alkyl of 1–6 carbon atoms, cycloalkyl of 3–6 carbon atoms, phenyl, naphthyl, heteroaryl or heterocycloalkyl;

$R_4$ is alkyl of 1–6 carbon atoms, alkenyl of 2–6 carbon atoms, alkynyl of 2–6 carbon atoms, cycloalkyl of 3–6 carbon atoms; perfluoroalkyl of 1–4 carbon atoms, phenyl, naphthyl, heteroaryl or heterocycloalkyl; and n is 0 to 2.

Suitable substituents of heterocycloalkyl groups of the present invention include, but are not limited to alkyl of 1–6 carbon atoms, cycloalkyl of 3–6 carbon atoms, phenyl, naphthyl, heteroaryl and heterocycloalkyl.

When a moiety contains more than substituent with the same designation each of those substituents may be the same or different.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

The compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stereoisomers and pharmaceutically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

The compounds of this invention are shown to inhibit the enzymes MMP-1, MMP-9, MMP-13 and TNF-α converting enzyme (TACE) and are therefore useful in the treatment of arthritis, tumor metastasis, tissue ulceration, abnormal wound healing, periodontal disease, graft rejection, insulin resistance, bone disease and HIV infection. In particular, the compounds of the invention provide enhanced levels of inhibition of the activity of TACE in vitro and in cellular assay and/or enhanced selectivity over MMP-1 and are thus particularly useful in the treatment of diseases mediated by TNF.

The invention is further directed to a process for making compounds of structure B involving one or more reactions as follows:

1) alkylating a compound of formula I, or a salt or solvate thereof,

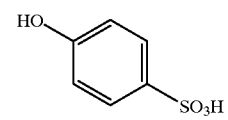

I into a compound of formula II

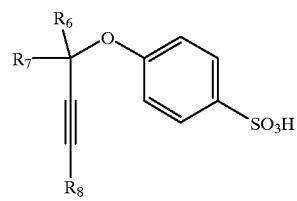

II 2) reacting a compound of formula II above, or a salt or solvate thereof, with a chlorinating agent such as thionyl chloride, chlorosulfonic acid, oxalyl chloride, phosphorus pentachloride, or other halogenating agents such as fluorosulfonic acid or thionyl bromide to a compound of formula III:

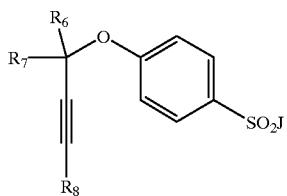

III wherein J is fluorine, bromine, chlorine.

The resultant sulfonyl chloride, fluoride or bromide, may be further converted into triazolide, imidazolide or benzothiazolide derivatives, where J is 1,2,4-triazolyl, benzotriazolyl or imidazol-yl, by reacting the compound with 1,2,4-triazole, imidazole or benzotriazole, respectively. $R_6$, $R_7$ and $R_8$ are as defined above.

The invention is still further directed to a process for making compounds of structure B involving one or more reactions as follows:

1) alkylating phenol, or a salt or solvate thereof, into a compound of formula IV:

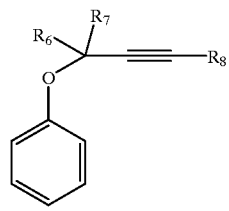

IV 2) reacting a compound of formula IV above, or a salt or solvate thereof with chlorosulfonic acid to prepare a compound of formula II above.

Particularly preferred intermediates are compounds of formulae II and III, with the proviso that R6 is not hydrogen.

The invention compounds are prepared using conventional techniques known to those skilled in the art of organic synthesis. The starting materials used in preparing the compounds of the invention are known, made by known methods or are commercially available. Some of the starting materials and intermediates, and methods for making said starting materials and intermediates are disclosed in U.S. Pat. No. 5,776,961.

Those skilled in the art will recognize that certain reactions are best carried out when other potentially reactive functionality on the molecule is masked or protected, thus avoiding undesirable side reactions and/or increasing the yield of the reaction. To this end, those skilled in the art may use protecting groups. Examples of these protecting group moieties may be found in T. W. Greene, P. G. M. Wuts "*Protective Groups in Organic Synthesis*", $2^{nd}$ Edition, 1991, Wiley & Sons, New York. Reactive side chain functionalities on amino acid starting materials are preferably protected. The need and choice of protecting groups for a particular reaction is known to those skilled in the art and depends on the nature of the functional group to be protected (hydroxy, amino, carboxy, etc.), the structure and stability of the molecule of which the substituent is part and the reaction conditions.

When preparing or elaborating compounds of the invention containing aryl, heteroaryl or heterocyclic rings, those skilled in the art recognize that substituents on that ring may be prepared before, after or concomitant with construction of the ring. For clarity, substituents on such rings have been omitted from the schemes herein below.

Those skilled in the art will recognize that the nature and order of the synthetic steps presented may be varied for the purpose of optimizing the formation of the compounds of the invention.

The hydroxamic acid compounds of the invention, 1, are prepared according to Scheme 1 by converting a carboxylic acid, 2, into the corresponding acid chloride or anhydride, or by reacting it with a suitable peptide coupling reagent, followed by reaction with hydroxylamine to give 1, or with a protected hydroxylamine derivative to give 3. Compounds 3, wherein $R_{30}$ is a t-butyl, benzyl, trialkylsilyl or other suitable masking group may then be deprotected by known methods to provide the hydroxamic acid 1.

Scheme 1

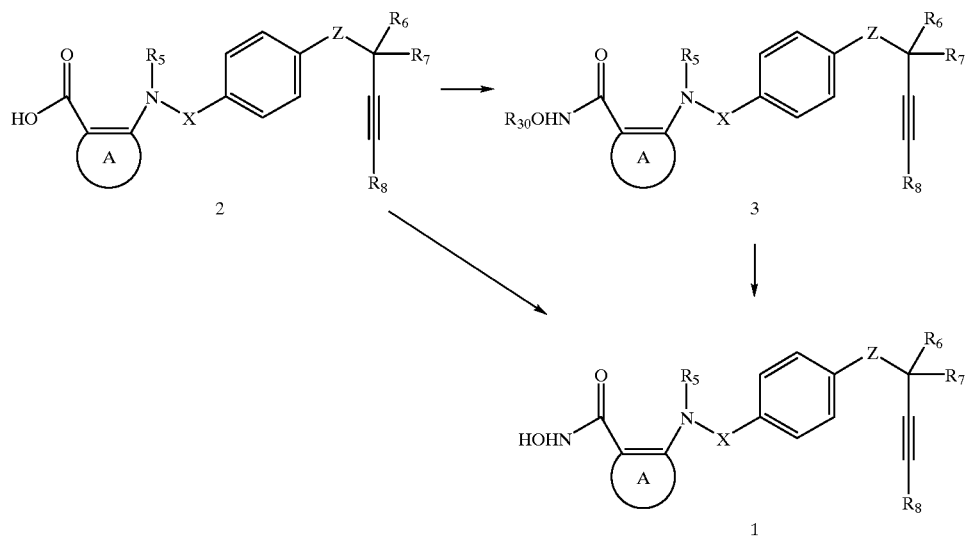

Carboxylic acids 2 may be prepared as shown in Scheme 2. Amino acid derivative 4, in which $R_{40}$ is hydrogen or a suitable carboxylic acid protecting group, may be sulfonylated or phosphorylated by reacting with compounds 5, in which J is a suitable leaving group including, but not limited to chlorine. The N—H compound 6 may then be alkylated with $R_3J$ and a base such as potassium carbonate or sodium hydride in a polar aprotic solvent such as acetone, N,N-dimethylformamide (DMF), or tetrahydrofuran (THF) to provide sulfonamide 7. Compound 7 is also available through direct reaction of 5 with an N-substituted amino acid derivative, 8. Conversion of 7 into the carboxylic acid is performed by acid, base hydrolysis, or other method consistent with the choice of protecting group $R_{40}$ and the presence of a carbon-carbon triple bond.

group such as halogen mesylate, tosylate, or triflate to give 11. Acetylenes 10 are commercially available or known compounds, or they may be synthesized by known methods by those skilled in the art. The sulfonic acid salts 11 may be converted into the corresponding sulfonyl chloride or other sulfonylating agent 5 by known methods, such as reaction with oxalyl chloride or other reagent compatible with substituents $R_6$, $R_7$ and $R_8$ and the acetylene. Alternatively, the disulfide 12 may be converted into di-acetylene 13 by reaction with compounds 10, followed by reduction of the disulfide bond to provide the analogous thiols which may be converted into 5 by known methods. Alkylation of the phenol, thiophenol, aniline or protected aniline 14 with 10 to give 15, followed by reaction with chlorosulfonic acid provide sulfonic acids 16 which are readily converted into 5

Scheme 2

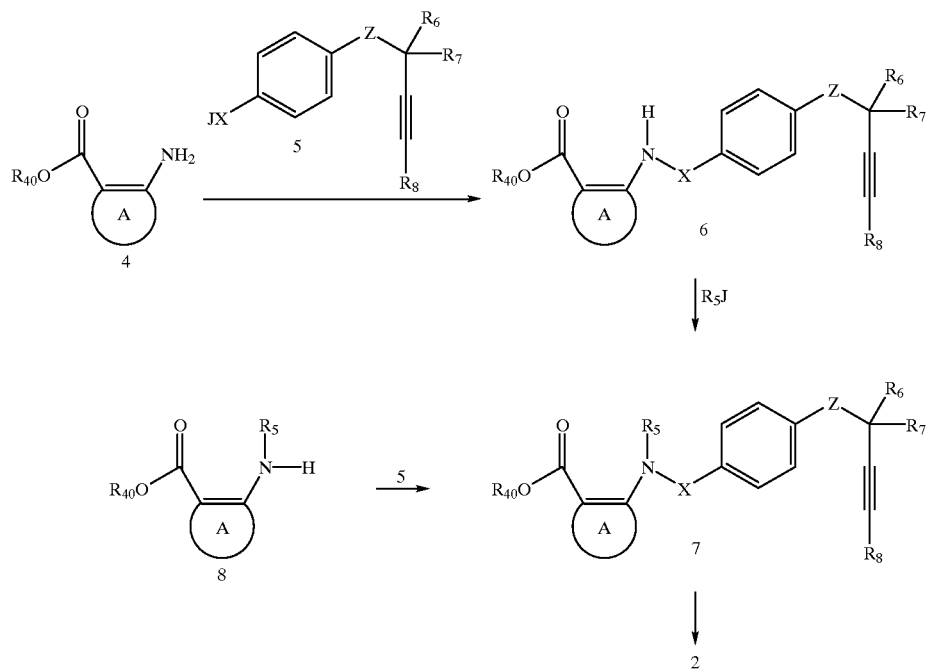

Methods of preparation of sulfonylating agents 5 are shown in Scheme 3. Thus, sulfonic acid salts 9, where $ZR_{50}$ is a hydroxy, thiol or substituted amino moiety may be alkylated with acetylenes 10, where J is a suitable leaving with oxalyl chloride or similar reagents. Thiophenols 17 are also precursors to S via protection of the thiol, alkylation of ZH, where Z is O, N or S, and deprotection of the sulfur followed by oxidation to the sulfonic acid 16.

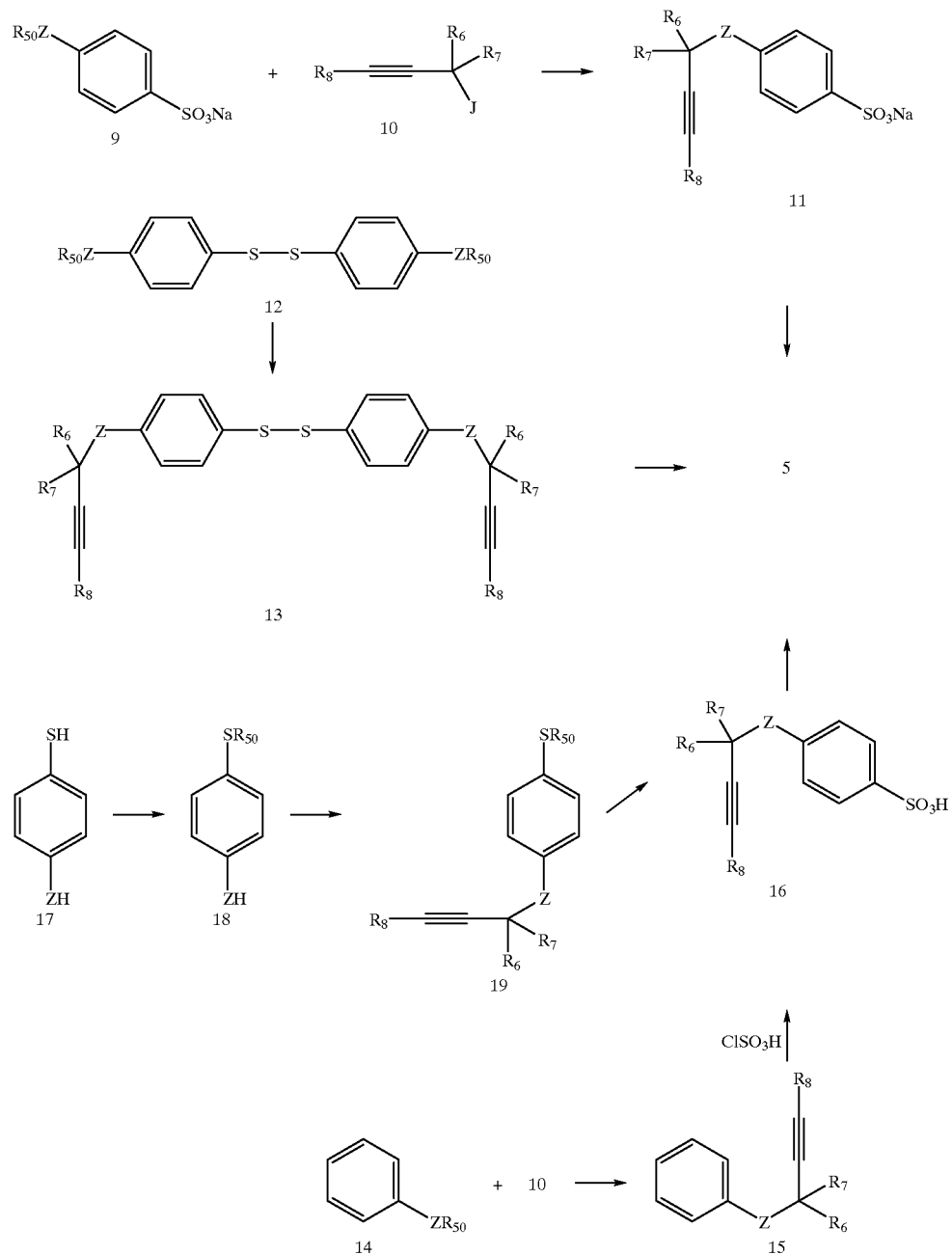
Scheme 3
The phosphorus containing analogs of 8 may be prepared using similar methodology, as shown in Scheme 4.

Scheme 4

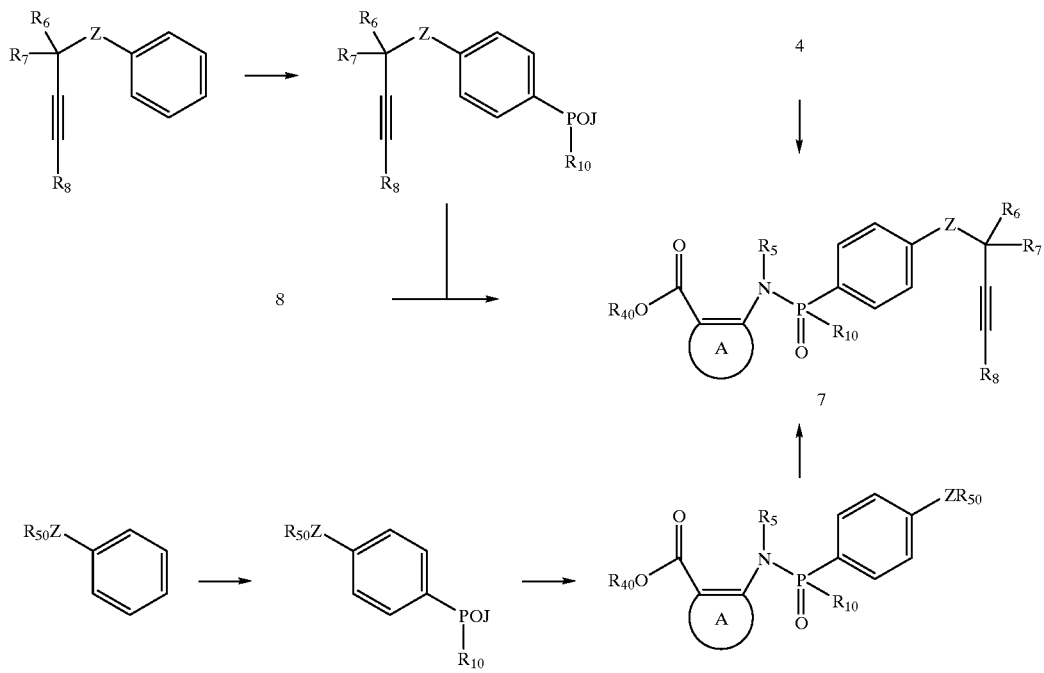

The acetylenic side chain may also be appended after sulfonylation or phosphorylation of the amino acid derivative, as shown in Scheme 5. Thus, the amino acid derivatives 4 and 8 can be sulfonylated or phosphorylated with compounds 20, where $ZR_{50}$ is hydroxy or protected hydroxy, thiol or amine, and, if necessary, alkylated with $R_7J$ as in Scheme 2, to give 21. Removal of the $R_{50}$ masking group to give 22 and subsequent alkylation of the resulting phenol, thiol or amine with 10 provides 7. In the case where $ZR_{50}$ is equal to OH, no deprotection step is required to give 22.

The propargylic amine analogs of 7 can be synthesized as shown in Scheme 6 starting from the amino acid derivatives 4 and/or 8. Sulfonylation or phosphorylation with para-nitro aryl compound 23, for example 4-nitrobenzenesulfonyl chloride, followed by alkylation with $R_5J$ (for 4) using a base such as potassium carbonate or sodium hydride in DMF provides 24. Reduction of the nitro moiety with hydrogen and palladium on carbon, tin chloride or other known method to give aniline 25 and subsequent alkylation with 10 then provides 7. Aniline 25 may be derivatized with a suitable nitrogen protecting group, such as t-butoxycarbonyl, to give 26 prior to alkylation with 10 subsequent deprotection after the alkylation step.

Scheme 5

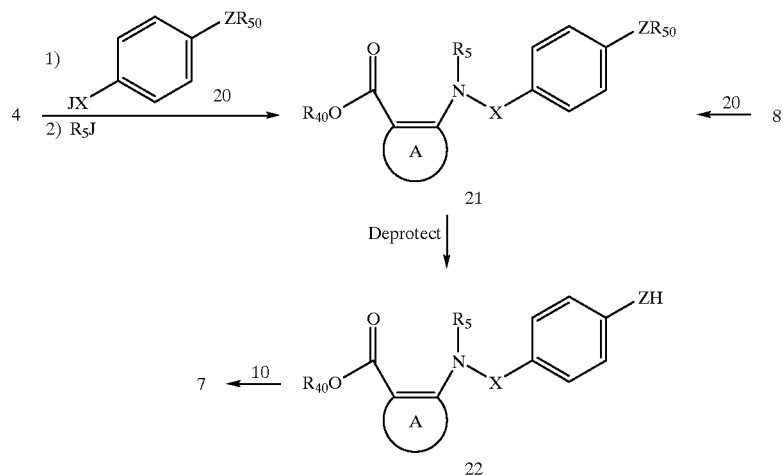

Scheme 6

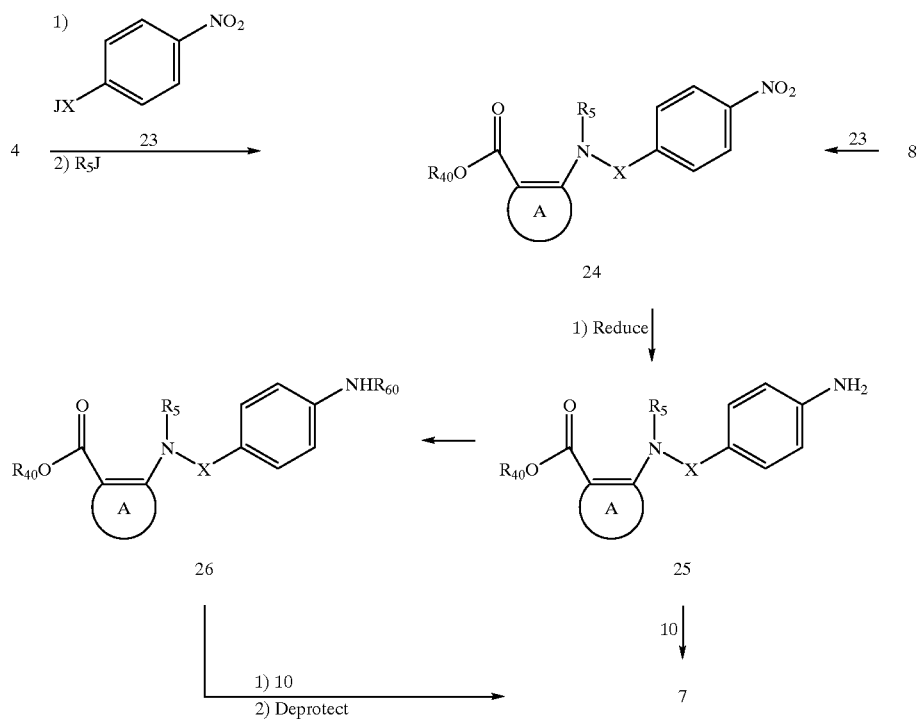

Acetylenic derivatives 7 are also accessible via the fluoro compounds 27, readily prepared from the amino acid derivatives 4 and/or 8 by reaction with fluoraryl 26, as shown in Scheme 7. Displacement of the fluorine of 27 in the presence of a base such as sodium hydride with a masked hydroxy, thiol, or amino group ($HZR_{70}$, where $R_{70}$ is a suitable protecting group) in a polar aprotic solvent such as DMF, followed by deprotection gives 28, which can then be alkylated with 10 to provide 7. Conversion of 27 to 28, where Z is sulfur, might also be accomplished with $Na_2S$, $K_2S$, NaSH or KS(C=S)OEt. The fluorine of 27 can also be displaced in a polar aprotic solvent with the propargylic derivative 29, where Z is O, S or NH, in the presence of a base such as sodium hydride, to give 7 directly.

Scheme 7

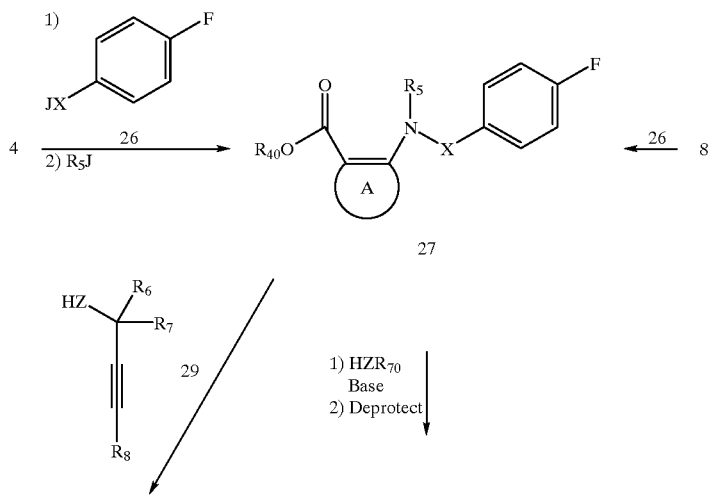

-continued

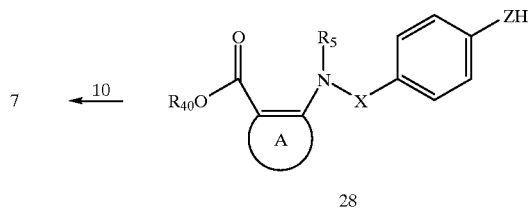

28

Compound 7, wherein Z is a methylene group, is available via 30, as shown in Scheme 8. Benzylic bromination of 30 with N-bromosuccinimide in a chlorinated hydrocarbon solvent provides bromide 31. This is followed by displacement of the bromide with the appropriate propynyl cuprate to provide sulfonamide 8.

Some of the methods available for the derivatization of compounds of structure 32 (equivalent to compound 7 wherein $R_{12}$ is hydrogen) are shown in Scheme 9. Metallation of the terminal acetylene 32 followed by addition of an aldehyde or alkyl halide, sulfonate or triflate provides derivatives 33 and 34. Reaction of 32 with formaldehyde Scheme 8

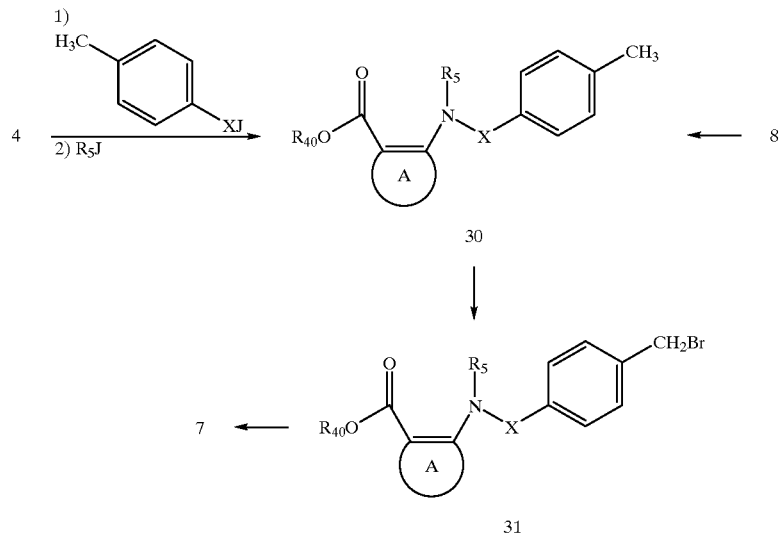

Compounds of the invention can also be prepared by modifying substituents on the acetylenic side chain at any stage after sulfonylation or phosphorylation of the starting amino acid derivatives 4 or 8. Functional groups such as halogen, hydroxy, amino, aldehyde, ester, ketone, etc. may be manipulated by standard methods to form the moieties defined by $R_1$–$R_8$ of compounds 1. It is recognized by those skilled in the art of organic synthesis that the successful use of these methods is dependent upon the compatibility of substituents on other parts of the molecule. Protecting groups and/or changes in the order of steps described herein may be required.

and an amine provides the Mannich addition product 35. Cyanogen bromide addition to 35 gives the propargylic bromide 36 which may be displaced with a variety of nucleophiles to give, for example, ethers, thioethers and amines 37. Palladium catalyzed coupling reactions of 32 provide the aryl or heteroaryl acetylenes 38. It is recognized by those skilled in the art of organic synthesis that the successful use of these methods is dependent upon the compatibility of substituents on other parts of the molecule. Protecting groups and/or changes in the order of steps described herein may be required.

Scheme 9

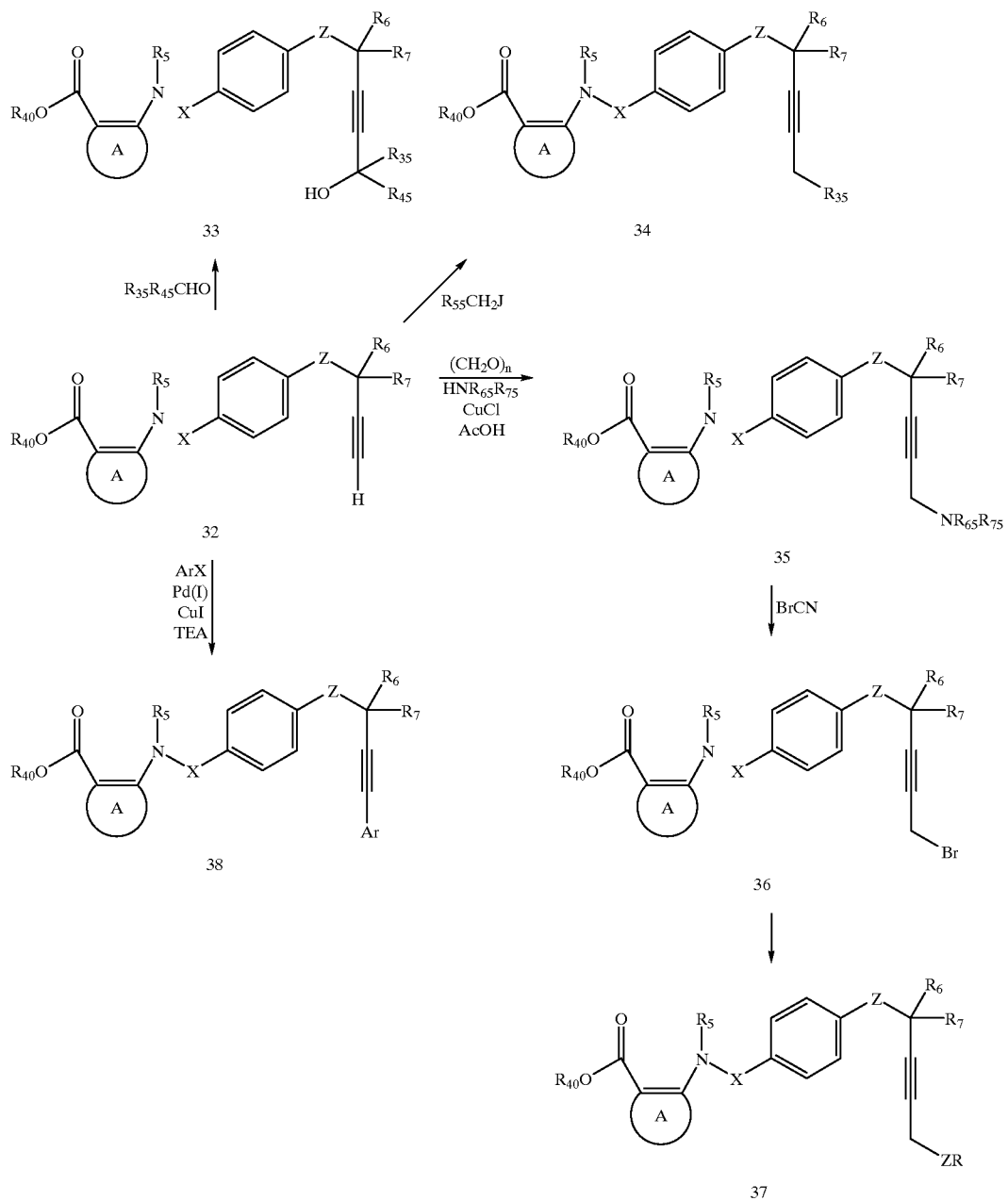

The following specific examples illustrate the preparation of representative compounds of this invention. The starting materials, intermediates, and reagents are either commercially available or can be readily prepared following standard literature procedures by one skilled in the art of organic synthesis.

EXAMPLE 1

3-Methyl-5-bromo-2-(4-fluoro-benzenesulfonylamino)-benzoic acid

To a solution of 25.0 g (0.102 mol) of 2-amino-3-methyl-5-bromobenzoic acid methyl ester (U.S. Pat. No. 5,776,961) in 300 mL of pyridine was added 21.93 g (0.113 mol) of 4-fluorobenzenesulfonyl chloride. The reaction mixture was stirred for 18 h at 80°, cooled to room temperature and poured into water. The resulting mixture was extracted with ethyl acetate and the combined organics were then washed with 5% HCl solution and water. The organic layer was then dried over $MgSO_4$, filtered and concentrated in vacuo. The residue was chromatographed on silica gel eluting with ethyl acetate/hexanes (1:3) to provide 14.53 g (39%) of the desired product as a tan solid. Electrospray Mass Spec: 388.0 (M–H)⁻

EXAMPLE 2

5-Bromo-2-[(4-fluoro-benzenesulfonyl)-methyl-amino]-3-methyl-benzoic acid methyl ester To a solution of 14.53 g (0.040 mol) of the product of Example 1 in 300 mL of DMF was added 66.1 g (0.479 mol)

of potassium carbonate followed by 9.94 mL (0.160 mol) of iodomethane. The resulting mixture was stirred at room temperature for 48 h and then diluted with water and ether. The organic layer was separated and washed with water and then dried over $MgSO_4$, filtered and concentrated in vacuo. The residue was chromatographed on silica gel eluting with ethyl acetate/hexanes (1:10) to provide 12.83 g (82%) of the desired product as a pale yellow solid. Electrospray Mass Spec: 415.8 $(M+H)^+$

EXAMPLE 3

5-Bromo-2-[(4-hydroxy-benzenesulfonyl)-methyl-amino]-3-methyl-benzoic acid

To a solution of 17.0 mL (0.227 mol) of 2-butyn-1-ol in 375 mL of DMF at room temperature was added 9.08 g (0.227 mol) of 60% sodium hydride. The resulting mixture was stirred for 0.5 h and then a solution of 17.8 g (0.045 mol) of the product of Example 2 dissolved in 50 mL of DMF was added to the reaction. The reaction mixture was then heated to reflux for 24 h, cooled to room temperature and then acidified to pH 2 with 10% HCl solution. After stirring for 1 h the resulting mixture was diluted with water and extracted with ethyl acetate. The combined organics were then dried over $MgSO_4$, filtered and concentrated in vacuo. The residue was chromatographed on silica gel eluting with ethyl acetate/hexanes (1:3) to provide 12.5 g (69%) of the desired phenol-carboxylic acid product as a white solid. Electrospray Mass Spec: 401.8 $(M+H)^+$

EXAMPLE 4

5-Bromo-2-[(4-hydroxy-benzenesulfonyl)-methyl-amino]-3-methyl-benzoic acid methyl ester To a solution of 15.2 g (0.038 mol) of the product of Example 3 in 125 mL of DMF was added 9.58 g (0.114 mol) of sodium bicarbonate followed by 4.7 mL (0.076 mol) of iodomethane. The resulting mixture was stirred at room temperature for 5 h and then diluted with ether and water. The organics were separated and washed with water, dried over $MgSO_4$, filtered and concentrated in vacuo. The residue was chromatographed on silica gel eluting with ethyl acetate/hexanes (1:3) to provide 12.27 g (78%) of the desired phenol-ester product as a pale yellow solid. Electrospray Mass Spec: 413.7 $(M+H)^+$

EXAMPLE 5

5-Bromo-3-methyl-2-[methyl-(4-prop-2-ynyloxy-benzenesulfonyl)-amino]-benzoic acid methyl ester To a solution of 0.317 g (1.208 mmol) of triphenylphosphine dissolved in 5 mL of benzene and 2 mL of THF was added 0.070 mL (1.208 mmol) of propargyl alcohol. After five minutes 0.500 g (1.208 mmol) of the product of Example 4, dissolved in 2 mL of THF, was added to the reaction followed by 0.190 mL (1.208 mmol) of diethyl azodicarboxylate. The resulting reaction mixture was stirred for 18 h at room temperature and then concentrated in vacuo. The residue was chromatographed on silica gel eluting with ethyl acetate/hexanes (1:10) to provide 0.389 g (71%) of the desired propargylic ether as a white solid. Electrospray Mass Spec: 451.8 $(M+H)^+$

EXAMPLE 6

5-Bromo-2-[(4-but-2-ynyloxy-benzenesulfonyl)-methyl-amino]-3-methyl-benzoic acid According to the procedure of Example 5 0.150 g (0.363 mmol) of the product of Example 4 was reacted with 0.027 mL (0.362 mmol) of 2-butyn-1-ol to give 0.106 g (63%) of the alkynyloxy ether.

The alkynyloxy ether was dissolved in 2.2 mL of THF/methanol (1:1) and 1.1 mL of 1.0N sodium hydroxide solution was added. The reaction was heated to reflux overnight, cooled to room temperature and acidified with 10% HCl solution. The mixture was extracted with ethyl acetate and the combined organics were dried over $MgSO_4$, filtered and concentrated in vacuo to provide 0.099 g (97%) of the desired carboxylic acid product as a white solid. Electrospray Mass Spec: 451.8 $(M+H)^+$

EXAMPLE 7

5-Bromo-3-methyl-2-[methyl-(4-pent-2-ynyloxy-benzenesulfonyl)-amino]-benzoic acid According to the procedure of Example 6 0.250 g (0.604 mmol) of the product of Example 4 was reacted with 0.056 mL (0.604 mmol) of 2-pentyn-1-ol to give 0.233 g of the ether-ester, followed by base hydrolysis to give 0.22 g (97%) of the carboxylic acid as a white solid. Electrospray Mass Spec: 465.9 $(M+H)^+$

EXAMPLE 8

5-Bromo-2-[(4-hept-2-ynyloxy-benzenesulfonyl)-methyl-amino]-3-methyl-benzoic acid According to the procedure of Example 6 0.250 g (0.604 mmol) of the product of Example 4 was reacted with 0.077 mL (0.604 mmol) of 2-heptyn-1-ol to give 0.246 g of the ether-ester, followed by base hydrolysis to give 0.214 g (90%) of the carboxylic acid as a white solid. Electrospray Mass Spec 494.0 $(M+H)^+$

EXAMPLE 9

5-Bromo-2-[(4-hex-2-ynyloxy-benzenesulfonyl)-methyl-amino]-3-methyl-benzoic acid methyl ester According to the procedure of Example 5 0.250 g (0.604 mmol) of the product of Example 4 was reacted with 0.059 g (0.604 mmol) of 2-hexyn-1-ol to give 0.206 g (69%) of the alkynyloxy ether. Electrospray Mass Spec 494.0 $(M+H)^+$

EXAMPLE 10

5-Bromo-2-[(4-hex-2-ynyloxy-benzenesulfonyl)-methyl-amino]-3-methyl-benzoic acid To a solution of 0.206 g (0.417 mmol) of the product of Example 9 dissolved in 4.0 mL of THF/methanol (1:1) and 0.5mL of 5.0N sodium hydroxide solution was added. The reaction was stirred overnight at room temperature and then acidified with 10% HCl solution. The mixture was extracted with dichloromethane and the combined organics were dried over $MgSO_4$, filtered and concentrated in vacuo to provide a white solid which was washed with ether/hexanes (1:1) and dried in vacuo to give 0.163 g (82%) of the desired carboxylic acid product as a white solid. Electrospray Mass Spec: 477.9 $(M-H)^-$

EXAMPLE 11

5-Bromo-3-methyl-2-{methyl-[4-(3-phenyl-prop-2-ynyloxy)-benzenesulfonyl]-amino}-benzoic acid methyl ester According to the procedure of Example 5 0.250 g (0.604 mmol) of the product of Example 4 was reacted with 0.080 g (0.604 mmol) of 3-phenyl propargyl alcohol to give 0.272 g (85%) of the alkynyloxy ether as a brown oil. Electrospray Mass Spec 527.8 (M+H)$^+$

EXAMPLE 12

5-Bromo-2-({4-[3-(3-methoxy-phenyl)-prop-2-ynyloxy]-benzenesulfonyl}-methyl-amino)-3-methyl-benzoic acid methyl ester According to the procedure of Example 5 0.250 g (0.604 mmol) of the product of Example 4 was reacted with 0.098 g (0.604 mmol) of 3-(3-methoxy)-phenyl propargyl alcohol to give 0.285 g (85%) of the alkynyloxy ether as a pale yellow oil. Electrospray Mass Spec 557.8 (M+H)$^+$

EXAMPLE 13

5-Bromo-2-({4-[3-(2-methoxy-phenyl)-prop-2-ynyloxy]-benzenesulfonyl}-methyl-amino)-3-methyl-benzoic acid methyl ester According to the procedure of Example 5 0.250 g (0.604 mmol) of the product of Example 4 was reacted with 0.098 g (0.604 mmol) of 3-(2-methoxy)-phenyl propargyl alcohol to give 0.296 g (88%) of the alkynyloxy ether as a colorless oil. Electrospray Mass Spec 557.8 (M+H)$^+$

EXAMPLE 14

5-Bromo-2-({4-[3-(4-methoxy-phenyl)-prop-2-ynyloxy]-benzenesulfonyl}-methyl-amino)-3-methyl-benzoic acid methyl ester According to the procedure of Example 5 0.250 g (0.604 mmol) of the product of Example 4 was reacted with 0.098 g (0.604 mmol) of 3-(4-methoxy)-phenyl propargyl alcohol to give 0.240 g (71%) of the alkynyloxy ether as a brown oil. Electrospray Mass Spec 557.8 (M+H)$^+$

EXAMPLE 15

5-Bromo-3-methyl-2-(methyl-{4-[4-(tetrahydro-pyran-2-yloxy)-but-2-ynyloxy]-benzenesulfonyl}-amino)-benzoic acid methyl ester According to the procedure of Example 5 0.500 g (1.208 mmol) of the product of Example 4 was reacted with 0.226 g (1.328 mmol) of 4-tetrahydropyran-2-butyn-1,4-diol to give 0.60 g (88%) of the alkynyloxy ether as a colorless oil. Electrospray Mass Spec 567.9 (M+H)$^+$

EXAMPLE 16

5-Bromo-2-{[4-(tert-butyl-dimethyl-silanyloxy)-benzenesulfonyl]-methyl-amino}-3-methyl-benzoic acid methyl ester To a solution of 1.25 g (3.019 mmol) of the product of Example 4 in 5.0 mL of DMF was added 0.514 g (7.548 mmol) of imidazole followed by 0.546 g (3.623 mmol) of t-butyldimethylsilyl chloride. The resulting mixture was stirred at room temperature for 15 h and then diluted with ether and water. The organics were washed with water, dried over Na$_2$SO$_4$, filtered and concentrated in vacuo. The residue was chromatographed on silica gel eluting with ethyl acetate/hexanes (1:10) to provide 1.34 g (84%) of the silyl ether as a white solid. Electrospray Mass Spec 527.8 (M+H)$^+$

EXAMPLE 17

2-[(4-But-2-ynyloxy-benzenesulfonyl)-methyl-amino]-5-iodo-3-methyl-benzoic acid methyl ester To a solution of 0.340 g (0.644 mmol) of the product of Example 16 in 30 mL of dioxane was added 1.30 mL (2.576 mmol) of bis(tributyltin) followed by 0.059 g (0.051 mmol) of tetrakis(triphenylphosphine)palladium(0). The resulting mixture was heated to reflux overnight and then concentrated in vacuo. The residue was chromatographed on silica gel eluting with ethyl acetate/hexanes (1:20) to provide 0.34 g (72%) of the desired aryl stannane.

The stannane was then dissolved in 50 mL of chloroform and 10 mL of a 0.1M solution of iodine in chloroform was added dropwise. After 15 minutes at room temperature the reaction was quenched with a solution of 1.5 g of potassium fluoride in 30 mL of methanol followed by 30 mL of 5% sodium bisulfite solution. The organic layer was separated, and the aqueous layer was extracted with dichloromethane. The combined organics were dried over Na$_2$SO$_4$, filtered and concentrated in vacuo. The residue was partitioned between hexanes and acetonitrile and the acetonitrile layer was then concentrated in vacuo to give 0.265 g (100%) of the crude aryl iodide.

The aryl iodide was dissolved in 5 mL of THF and 1.0 mL of a 1.0M solution of tetrabutylammonium fluoride in THF was added. The reaction was stirred for 1 h at room temperature and the acidified with 5% HCl solution and extracted with dichloromethane. The combined organics were dried over MgSO$_4$, filtered and concentrated in vacuo to provide 0.185 g (87%) of the phenol.

According to the procedure of Example 5 0.185 g (0.401 mmol) of the phenol and 0.030 mL of 2-butyn-1-ol provided 0.143 g (69%) of the desired ether as a colorless oil. Electrospray Mass Spec 513.8 (M+H)$^+$

EXAMPLE 18

2-[Benzyl-(4-hydroxy-benzenesulfonyl)-amino]-3,5-dimethyl-benzoic acid

According to the procedure of Example 3 1.360 g (3.185 mmol) of 2-[benzyl-(4-fluoro-benzenesulfonyl)-amino]-3,5-dimethyl-benzoic acid methyl ester (U.S. Pat. No. 5,776,961) gives 0.956 g (73%) of the phenol-carboxylic acid as a white solid after trituration with ether. Electrospray Mass Spec 411.9 (M+H)$^+$

EXAMPLE 19

2-[Benzyl-(4-hydroxy-benzenesulfonyl)-amino]-3,5-dimethyl-benzoic acid methyl ester To a solution of 0.820 g (1.995 mmol) of the product of Example 18 in 10 mL of DMF was added 0.826 g (5.985 mmol) of potassium carbonate followed by 0.124 mL (1.995 mmol) of iodomethane. The reaction was stirred at room temperature for 2 h and then diluted with ether and water and acidified with 5% HCl solution. The Aqueous layer was extracted with ethyl acetate and the combined organics were dried over MgSO$_4$, filtered and concentrated in vacuo. The residue was chromatographed on silica gel eluting with ethyl acetate/hexanes (1:3) to provide 0.090 g (87%) of the phenol-ester. Electrospray Mass Spec 425.9 (M+H)$^+$

EXAMPLE 20

2-[Benzyl-(4-but-2-ynyloxy-benzenesulfonyl)-amino]-3,5-dimethyl-benzoic acid methyl ester According to the procedure of Example 5 0.250 g (0.588 mmol) of the product of Example 19 was reacted with 0.44 mL (0.588 mmol) of 2-butyn-1 ol to give 0.203 g (72%) of the alkynyloxy ether as a white solid. Electrospray Mass Spec 477.9 (M+H)$^+$

EXAMPLE 21

5-Bromo-2-[(4-hydroxy-benzenesulfonyl)-(4-methyl-piperazin-1-ylmethyl)-amino]-3-methyl-benzoic acid methyl ester To a solution of 1.0 g (1.894 mmol) of the product of Example 16 in 60 mL of carbon tetrachloride was added 0.405 g of N-bromosuccinimide. The resulting mixture was heated to reflux for 2 h while being irradiated by a sun lamp. The reaction was then cooled top room temperature, washed with water, dried over $Na_2SO_4$, filtered and concentrated in vacuo.

The residue was dissolved in 5.0 mL of DMF and 0.784 g (5.682 mmol) of potassium carbonate was added followed by 0.21 mL (1.894 mmol) of 1-methylpiperazine. The resulting mixture was stirred for 48 h at room temperature and then diluted with water and ethyl acetate. The organics were washed with water and then extracted with 10% HCl solution. The acid layer was neutralized with 1.0N NaOH solution and extracted with dichloromethane. The combined dichloromethane extracts were dried over $Na_2SO_4$, filtered and concentrated in vacuo to provide 0.501 g (52%) of the piperazine-phenol as a white solid. Electrospray Mass Spec 511.9 $(M+H)^+$

EXAMPLE 22

5-Bromo-2- [(4-but-2-ynyloxy-benzenesulfonyl)-methyl-amino]-3-(4-methyl-piperazin-1-ylmethyl)-benzoic acid methyl ester To a solution of 0.963 g (3.672 mmol) of triphenylphosphine in 5.0 mL of THF was added 0.275 mL (3.672 mmol) of 2-butyn-1-ol followed by 0.376 g (0.734 mmol) of the product of Example 21 dissolved in 2 mL of dichloromethane. After 5 minutes at room temperature 0.578 mL (3.672 mmol) of diethyl azodicarboxylate was added dropwise and the resulting reaction mixture was stirred overnight at room temperature and then concentrated in vacuo. The residue was diluted with ethyl acetate and the organics were extracted with 10% HCl solution. The combined acid extracts were basified with 1.0N NaOH solution and then extracted with dichloromethane. The combined dichloromethane extracts were dried over $Na_2SO_4$, filtered and concentrated in vacuo. The residue was chromatographed on silica gel eluting with dichloromethane/methanol/triethylamine (100:2:0.5) to provide 0.149 g (36%) of the butynyl ether as a pale yellow oil. Electrospray Mass Spec 563.9 $(M+H)^+$

EXAMPLE 23

5-Bromo-3-methyl-2-{methyl-[4-(4-pyrrolidin-1-yl-but-2-ynyloxy)-benzenesulfonyl]-aniino}-benzoic acid methyl ester To a solution of 0.300 g (0.664 mmol) of the product of Example 5 in 2.0 mL of dioxane was added 0.054 g (1.659 mmol) of paraformaldehyde, 0.111 mL (1.327 mmol) of pyrrolidine, 0.245 mL of acetic acid and 2.5 mg of cuprous chloride. The resulting mixture was stirred at room temperature for 15 minutes and then heated to reflux for 2 h. After cooling to room temperature the reaction mixture was extracted with 10% HCl solution and the aqueous extracts were then basified with 1.0N NaOH solution and extracted with ether. The combined ether extracts were dried over $Na_2SO_4$, filtered and concentrated in vacuo to provide 0.216 g (61%) of the pyrrolidine-alkyne as a brown oil. Electrospray Mass Spec 520.9 $(M+H)^+$

EXAMPLE 24

5-Bromo-2-{[4-(4-diethylamino-but-2-ynyloxy)-benzenesulfonyl]-methyl-amino}-3-methyl-benzoic acid methyl ester According to the procedure of Example 23 1.00 g (2.212 mmol) of the product of Example 5 provides 0.749 g (63%) of the diethylamino-alkyne as a yellow oil after chromatography on silica gel eluting with ethyl acetate. Electrospray Mass Spec 536.9 $(M+H)^+$

EXAMPLE 25

5-Bromo-2-{[4-(4-bromo-but-2-ynyloxy)-benzenesulfonyl]-methyl-amino}-3-methyl-benzoic acid methyl ester To a 0° solution of 0.707 g (1.317 mmol) of the product of Example 24 dissolved in 10 mL of ether was added 0.53 mL of a 3.0M solution of cyanogen bromide in dichloromethane. The reaction was warmed to room temperature and stirred overnight. The reaction mixture was then filtered and the filtrate was diluted with ether, washed with 5% HCl solution and brine. The organics were dried over $Na_2SO_4$, filtered and concentrated in vacuo to provide 0.628 g (88%) of the propargylic bromide as a light brown oil.

EXAMPLE 26

5-Bromo-2-{[4-(4-methoxy-but-2-ynyloxy)-benzenesulfonyl]-methyl-amino}-3-methy-l-benzoic acid To a solution of 0.117 g (0.215 mmol) of the product of Example 25 in 1.0 mL of THF and 3.0 mL of methanol was added 0.5 mL of a 5.0N solution of sodium hydroxide followed by 3.6 mg of tetrabutylammonium hydrogen sulfate. The resulting reaction mixture was stirred at room temperature for 15 h and then acidified with 10% HCl solution and extracted with dichloromethane. The combined organics were dried over $MgSO_4$, filtered and concentrated in vacuo to provide 0.083 g (81%) of the bis-propargylic ether carboxylic acid as a white solid. Electrospray Mass Spec 481.8 $(M+H)^+$

EXAMPLE 27

5-Bromo-2-{[4-(4-cyclobutylamino-but-2-ynyloxy)-benzenesulfonyl]-methyl-amino}-3-methyl-benzoic acid methyl ester To a solution of 0.300 g (0.550 mmol) of the product of Example 25 in 3.0 mL of THF was added 0.103 mL (1.211 mmol) of cyclobutylamine and the reaction was stirred for 15 h at room temperature. The resulting mixture was diluted with ether and the organics were washed with water and brine, dried over $Na_2SO_4$, filtered and concentrated in vacuo. The residue was chromatographed on silica gel eluting with a gradient of ethyl acetate hexanes (1:1) to chloroform/methanol (9:1) to provide 0.199 g (69%) of the propargylic cyclobutylamine as a colorless oil. Electrospray Mass Spec 535.0 $(M+H)^+$

EXAMPLE 28

(4-{4-[(4-Bromo-2-hydroxycarbamoyl-6-methyl-phenyl)-methyl-sulfamoyl]-phenoxy}-but-2-ynyl)-cyclobutyl-carbamic acid tert-butyl ester To a solution of 0.167 g (0.312 mmol) of the product of Example 27 in 2.0 mL of DMF was added 0.075 g (0.343 mmol) of di-t-butyl dicarbonate and 7.6 mg of 4-dimethylaminopyridine. The reaction was stirred for 15 h at room temperature and then diluted with ether and washed with water, 5% HCl solution and brine. The organics were then dried over $Na_2SO_4$, filtered and concentrated in vacuo to provide 0.173 g (87%) of the carbamate.

To a solution of 0.173 g (0.272 mmol) of the t-butyl carbamate dissolved in 6.0 mL of THF/methanol (1:1) was added 1.4 mL of a 1.0N NaOH solution and the reaction mixture was then heated to reflux for 15 h. After cooling to room temperature the reaction mixture was acidified with 5% HCl solution and extracted with dichloromethane. The combined organics were dried over $MgSO_4$, filtered and concentrated in vacuo. The residue was chromatographed on silica gel eluting with ethyl acetate/hexanes (1:1) to provide 0.149 g (88%) of the carboxylic acid as a white solid.

To a 0° solution of 0.040 mL (0.792 mmol) of a 2.0M solution of oxalyl chloride in dichloromethane, dissolved in 3.4 mL of dichloromethane, was added 0.061 mL (0.792 mmol) of DMF and the mixture was stirred at 0° for 15 minutes. A solution of 0.164 g of the carboxylic acid, dissolved in 1 mL of DMF, was then added and the reaction was warmed to room temperature. The resulting mixture is stirred for 1 h at room temperature and then poured into a 0° mixture of 0.8 mL of water, 4.0 mL of THF and 0.25 mL of a 50% aqueous solution of hydroxylamine. The reaction is allowed to warm to room temperature overnight and the organics are then concentrated in vacuo. The residue is diluted with ethyl acetate, washed with water and saturated sodium bicarbonate, dried over $Na_2SO_4$, filtered and concentrated in vacuo to provide 0.153 g (91%) of the carbamate-hydroxamic acid as a white foam. Electrospray Mass Spec 637.9 $(M+H)^+$

EXAMPLE 29

5-Bromo-3-methyl-2-{methyl-[4-(4-methylamino-but-2-ynyloxy)-benzenesulfonyl]-amino}-benzoic acid methyl ester According to the procedure of Example 27 0.325 g (0.596 mmol) of the product of Example 25 reacted with methylamine to provide 0.132 g (45%) of the propargylic methylamine as a brown oil. Electrospray Mass Spec 495.0 $(M+H)^+$

EXAMPLE 30

(4-{4-[(4-Bromo-2-hydroxycarbamoyl-6-methyl-phenyl)-methyl-sulfamoyl]-phenoxy}-but-2-ynyl)-methyl-carbamic acid tert-butyl ester According to the procedure of Example 28 0.110 g (0.222 mmol) of the product of Example 29 was converted into 0.090 g of the carbamate-hydroxamic acid. Electrospray Mass Spec 598.0 $(M+H)^+$

EXAMPLE 31

5-Bromo-2-{[4-(4-cyclobutylamino-but-2-ynyloxy)-benzenesulfonyl]-methyl-amino}-N-hydroxy-3-methyl-benzamide To a solution of 0.100 g (0.157 mmol) of the product of Example 28 in 2.0 mL of dichloromethane was added 1.0 mL of trifluoroacetic acid. The resulting solution was stirred at room temperature for 1 h and then concentrated in vacuo. The residue was diluted with dichloromethane and washed with saturated sodium bicarbonate solution, dried over $Na_2SO_4$, filtered and concentrated in vacuo to provide 0.083 g (99%) of the amino-hydroxamic acid.

To a solution of 0.078 g (0.146 mmol) of the amino-hydroxamic acid dissolved in 2.0 mL of dichloromethane was added 0.29 mL (0.29 mmol) of a 1.0M solution of HCl in ether. The resulting mixture was stirred for 1 h at room temperature and then diluted with ether. The precipitate was filtered, washed with ether and dried in vacuo to provide 0.068 g (82%) of the hydrochloride salt of the amino-hydroxamic acid as a tan solid. Electrospray Mass Spec 535.8 $(M+H)^+$

EXAMPLE 32

5-Bromo-N-hydroxy-3-methyl-2-{methyl-[4-(4-methylamino-but-2-ynyloxy)-benzenesulfonyl]-amino}-benzamide According to the procedure of Example 31 0.066 g (0.111 mmol) of the product of Example 30 provides 0.042 g of the desired hydrochloride salt of the amino-hydroxamic acid. Electrospray Mass Spec 495.8 $(M+H)^+$

EXAMPLE 33

5-Bromo-2-({4-[4-(3-dimethylamino-propylamino)-but-2-ynyloxy]-benzenesulfonyl}-methyl-amino)-N-hydroxy-3-methyl-benzamide According to the procedure of Example 27 0.300 g (0.550 mmol) of the product of Example 25 reacted with 0.362 mL (2.75 mmol) of dimethylamino propylamine to provide 0.076 g (24%) of the propargylic diamine-ester.

According to the procedure of Example 28 0.135 g (0.239 mmol) of the diamine-ester was converted to the t-butyl carbamate, followed by hydrolysis of the ester and conversion of the carboxylic acid into 0.059 g of the carbamate-hydroxamic acid.

According to the procedure of Example 31 0.058 g of the carbamatehydroxamic acid was converted into 0.037 g of the desired bis-hydrochloride salt of the diamino-hydroxamic acid, obtained as a brown solid. Electrospray Mass Spec 569.0 $(M+H)^+$

EXAMPLE 34

5-Bromo-2-({4-[4-(2-dimethylamino-ethylamino)-but-2-ynyloxy]-benzenesulfonyl}-methyl-amino)-N-hydroxy-3-methyl-benzamide According to the procedure of Example 27 0.300 g (0.550 mmol) of the product of Example 25 reacted with 0.302 mL (2.75 mmol) of N,N-dimethylethylenediamine to provide 0.114 g (38%) of the propargylic diamine-ester.

According to the procedure of Example 28 0.192 g (0.348 mmol) of the diamine-ester was converted to the t-butyl carbamate, followed by hydrolysis of the ester and conversion of the carboxylic acid into 0.073 g of the carbamate-hydroxamic acid.

According to the procedure of Example 31 0.057 g of the carbamatehydroxamic acid was converted into 0.040 g of the desired bis-hydrochloride salt of the diamino-hydroxamic acid, obtained as a brown solid. Electrospray Mass Spec 553.0 $(M+H)^+$

EXAMPLE 35

5-Bromo-2-[(4-methoxy-benzenesulfonyl)-methyl-amino]-3-methyl-benzoic acid methyl ester To a solution of 5.00 g (0.012 mol) of 5-bromo-2-(4-methoxy-benzenesulfonylamino)-3-methyl-benzoic acid methyl ester (U.S. Pat. No. 5,776,961) in 40 mL of DMF was added 0.604 g (0.015 mol) of 60% sodium hydride. The resulting mixture was stirred at room temperature foe 0.5 h and then 1.2 ml (0.018 mol) of iodomethane was added. The reaction was then stirred for 15 h and then diluted with ether. The organics were washed with water, dried over $MgSO_4$, filtered and concentrated in vacuo. The residue was triturated with ether and the resulting white solid was collected by filtration and dried in vacuo to provide 4.45 g (86%) of the N-methyl sulfonamide. Electrospray Mass Spec 429.8 $(M+H)^+$

EXAMPLE 36

5-Bromo-N-hydroxy-2-[(4-methoxy-benzenesulfonyl)-methyl-amino]-3-methyl-benzamide To a solution of 0.200 g (0.467 mmol) of the product of Example 35 in 6.0 mL of THF/methanol (1:1) was added 2.3mL of 1.0N sodium hydroxide solution. The reaction was heated to reflux overnight, cooled to room temperature and acidified with 5% HCl solution. The mixture was extracted with ethyl acetate, washed with brine and the combined organics were then dried over $MgSO_4$, filtered and concentrated in vacuo. The residue was triturated with ether/hexanes (1:1) and the solid was collected and dried in vacuo to provide 0.136 g (70%) of the desired carboxylic acid product as a white solid.

To a 0° solution of 0.036 mL (0.710 mmol) of a 2.0M solution of oxalyl chloride in dichloromethane, diluted with 3.1 mL of dichloromethane, is added 0.055 mL (0.710 mmol) of DMF and the reaction is stirred for 15 minutes at 0°. A solution of 0.098 g (0.237 mmol) of the carboxylic acid, dissolved in 1 mL of DMF, was added to the reaction and the resulting mixture is stirred for 1 h at room temperature and then poured into a 0° mixture of 0.7 mL of water, 3.6 mL of THF and 0.23 mL of a 50% aqueous solution of hydroxylamine. The reaction is allowed to warm to room temperature overnight and the organics are then concentrated in vacuo. The residue is diluted with ethyl acetate, washed with 5% HCl solution, water and saturated sodium bicarbonate, dried over over $Na_2SO_4$, filtered and concentrated in vacuo to provide 0.081 g (79%) of the hydroxamic acid as a white foam. Electrospray Mass Spec 428.8 $(M+H)^+$

EXAMPLE 37

5-Bromo-2-[(4-butoxy-benzenesulfonyl)-methyl-amino]-3-methyl-benzoic acid methyl ester According to the procedure of Example 5 0.250 g (0.604 mmol) of the product of Example 4 was reacted with 0.055 mL (0.604 mmol) of n-butanol to give 0.241 g (85%) of the n-butyl ether. Electrospray Mass Spec 469.8 $(M+H)^+$

EXAMPLE 38

5-Bromo-2-[(4-butoxy-benzenesulfonyl)-methyl-amino]-3-methyl-benzoic acid

To a solution of 0.204 g (0.434 mmol) of the product of Example 37 in 6.0 mL of THF/methanol (1:1) was added 2.2mL of 1.0N sodium hydroxide solution. The reaction was heated to reflux overnight, cooled to room temperature and acidified with 5% HCl solution. The mixture was extracted with ethyl acetate, washed with brine and the combined organics were then dried over $MgSO_4$, filtered and concentrated in vacuo. The residue was triturated with ether/hexanes (1:1) and the solid was collected and dried in vacuo to provide 0.206 g (104%) of the desired carboxylic acid product as a white solid. Electrospray Mass Spec: 455.8 $(M+H)^+$

EXAMPLE 39

5-Bromo-2-[(4-butoxy-benzenesulfonyl)-methyl-amino]-N-hydroxy-3-methyl-benzamide To a 0° solution of 0.54 mL (1.072 mmol) of a 2.0M solution of oxalyl chloride in dichloromethane, diluted with 4.7 mL of dichloromethane, is added 0.083 mL (1.072 mmol) of DMF and the reaction is stirred for 15 minutes at 0° C. A solution of 0.163 g (0.357 mmol) of the carboxylic acid product of Example 38, dissolved in 1 mL of DMF, was added to the reaction and the resulting mixture is stirred for 1 h at room temperature and then poured into a 0° mixture of 1.0 mL of water, 5.4 mL of THF and 0.34 mL of a 50% aqueous solution of hydroxylamine. The reaction is allowed to warm to room temperature overnight and the organics are then concentrated in vacuo. The residue is diluted with ethyl acetate, washed with 5% HCl solution, water and saturated sodium bicarbonate, dried over $Na_2SO_4$, filtered and concentrated in vacuo to provide 0.157 g (93%) of the hydroxamic acid as a white foam. Electrospray Mass Spec 506.8 $(M+H)^+$

EXAMPLE 40

4-Amino-5-methyl-biphenyl-3-carboxylic acid methyl ester

To a solution of 5.0 g (0.021 mol) of 2-amino-5-bromo-3-methyl-benzoic acid methyl ester and 2.8 g (0.023 mol) of phenyl boronic acid in 150 mL of dimethoxyethane was added 20.5 mL of a 2.0M aqueous solution of $Na_2CO_3$ and 1.18 g (1.02 mmol) of $Pd(PPh_3)_4$. The reaction mixture was evacuated and filled with $N_2$ three times and was then heated to reflux overnight. The reaction was then cooled to room temperature, and poured into ethyl acetate and water. The aqueous layer was extracted three times with ethyl acetate. The combined organics were washed with brine, dried over $MgSO_4$ and concentrated in vacuo. The residue was chromatographed on silica gel using gradient elution (100% hexane to 4/1 hexane/ethyl acetate) to provide 2.5 g (50%) of 4-amino-5-methyl-biphenyl-3-carboxylic acid methyl ester. Electrospray Mass Spec: 241.8 $(M+H)^+$

EXAMPLE 41

5-Methyl-4-[4-(pyridin-4-yloxy)-benzenesulfonylamino]-biphenyl-3-carboxylic acid methyl ester To a solution of 1.43 g (5.93 mmol) of the product of Example 40 in 20 mL of pyridine was added 1.98 g (6.52 mmol) 4-(pyridin-4-yloxy)-benzenesulfonyl chloride and the reaction was stirred overnight. Additional 4-(pyridin-4-yloxy)-benzenesulfonyl chloride (0.5 g, 1.6 mmol) was added twice over the next two days. The reaction was then diluted with water and extracted three times with dichloromethane. The organics were combined, washed with brine, dried over $Na_2SO_4$, concentrated in vacuo and chromatographed on silica gel using gradient elution (100% hexane to 100% ethyl acetate) to provide 5-methyl-4-[4-(pyridin-4-yloxy)-benzenesulfonylamino]-biphenyl-3-carboxylic acid methyl ester 2.54 g (90%) as a white solid. Electrospray Mass Spec: 475.2 $(M+H)^+$

EXAMPLE 42

4-[(4-Hydroxy-benzenesulfonyl)-methyl-amino]-5-methyl-biphenyl-3-carboxylic acid methyl ester To a 0° C. solution of 1.25 g (2.63 mmol) of the product of Example 41 in 7 mL of DMF at was added 0.132 g (3.29 mmol) of 60% sodium hydride. The reaction was held at 0° C. for 15 minutes and then warmed to room temperature. Iodomethane (0.49 mL, 7.89 mmol) was added and the reaction was stirred overnight. The reaction mixture was quenched by the addition of water and the aqueous layer was extracted three times with dichloromethane. The organics were combined, washed with water and brine, dried over $MgSO_4$, and concentrated in vacuo to provide 0.9 g (68%) of 5-methyl-4-[4-(1-methylpyridinium-4-oxy-benzenesulfonyl)-methyl-amino]-biphenyl-3-carboxylic acid methyl ester iodide as a yellow solid. Electrospray Mass Spec: 503.1 $(M+H)^+$ To a solution of 0.4 g (0.79 mmol) of the pyridinium salt in $THF:MeOH:H_2O$ (2:1:1, 3 mL total) was added 0.037 g (0.88 mmol) of lithium hydroxide and the reaction was heated to reflux overnight. The reaction was neutralized with 6M HCl solution and extracted three times with ethyl acetate. The organics were combined, washed with brine, dried over $MgSO_4$, and concentrated in vacuo to provide 282 mg (86%) of 4-[(4-hydroxy-benzenesulfonyl)-methyl-amino]-5-methyl-biphenyl-3-carboxylic acid methyl ester. Electrospray Mass Spec: 412.0 $(M+H)^+$

EXAMPLE 43

4-[(4-But-2-ynyloxy-benzenesulfonyl)-methyl-amino]-5-methyl-biphenyl-3-carboxylic acid hydroxyamide According to the procedure of Example 5 242 mg (0.58 mmol) of the product of Example 42 and 0.049 ml (0.65 mmol) of 2-butyn-1-ol provides 0.239 g (98%) of 4-[(4-but-2-ynyloxy-benzenesulfonyl)-methyl-amino]-5-methyl-biphenyl-3-carboxylic acid methyl ester. Electrospray Mass Spec: 464.2 (M+H)+.

According to the procedure of Example 38 0.239 g (0.58 mmol) of the ester was hydrolyzed to provide 0.2 g (76%) of 4-[(4-but-2-ynyloxy-benzenesulfonyl)-methyl-amino]-5-methyl-biphenyl-3-carboxylic acid. Electrospray Mass Spec: 448.3.0 (M−H)−

According to the procedure of Example 39 0.20 g (0.44 mmol) of the carboxylic acid was converted to the hydroxamic acid 4-[(4-But- 2-ynyloxy-benzenesulfonyl)-methyl-amino]-5-methyl-biphenyl-3-carboxylic acid hydroxyamide providing 0.150 g (73%) of pure product. Electrospray Mass Spec: 465.0 $(M+H)^+$

EXAMPLE 44

5-Bromo-3-methyl-2-{methyl-[4-(3-phenyl-prop-2-ynyloxy)-benzenesulfonyl]-amino}-benzoic acid To a solution of 0.240 g (0.455 mmol) of the product of Example 11 in 6.0 mL of THF/methanol (1:1) was added 2.3mL of 1.0N sodium hydroxide solution. The reaction was heated to reflux overnight, cooled to room temperature and acidified with 5% HCl solution. The mixture was extracted with ethyl acetate, washed with brine and the combined organics were then dried over $MgSO_4$, filtered and concentrated in vacuo. The residue was triturated with ether/hexanes (1:1) and the solid was collected and dried in vacuo to provide 0.181 g (77%) of the desired carboxylic acid product as a white solid. Electrospray Mass Spec: 513.7 $(M+H)^+$

EXAMPLE 45

5-Bromo-2-({4-[3-(3-methoxy-phenyl)-prop-2-ynyloxy]-benzenesulfonyl}-methyl-amino)-3-methyl-benzoic acid To a solution of 0.251 g (0.450 mmol) of the product of Example 12 in 6.0 mL of THF/methanol (1:1) was added 2.3mL of 1.0N sodium hydroxide solution. The reaction was heated to reflux overnight, cooled to room temperature and acidified with 5% HCl solution. The mixture was extracted with ethyl acetate, washed with brine and the combined organics were then dried over $MgSO_4$, filtered and concentrated in vacuo. The residue was triturated with ether/hexanes (1:1) and the solid was collected and dried in vacuo to provide 0.184 g (75%) of the desired carboxylic acid product as a pale yellow solid. Electrospray Mass Spec: 543.8 $(M+H)^+$

EXAMPLE 46

5-Bromo-2-({4-[3-(2-methoxy-phenyl)-prop-2-ynyloxy]-benzenesulfonyl}-methyl-amino)-3-methyl-benzoic acid To a solution of 0.264 g (0.473 mmol) of the product of Example 13 in 6.0 mL of THF/methanol (1:1) was added 2.4 mL of 1.0N sodium hydroxide solution. The reaction was heated to reflux overnight, cooled to room temperature and acidified with 5% HCl solution. The mixture was extracted with ethyl acetate, washed with brine and the combined organics were then dried over $MgSO_4$, filtered and concentrated in vacuo. The residue was triturated with ether/hexanes (1:1) and the solid was collected and dried in vacuo to provide 0.159 g (62%) of the desired carboxylic acid product as a white solid. Electrospray Mass Spec: 543.8 $(M+H)^+$

EXAMPLE 47

5-Bromo-2-({4-[3-(4-methoxy-phenyl)-prop-2-ynyloxy]-benzenesulfonyl}-methyl-amino)-3-methyl-benzoic acid To a solution of 0.217 g (0.389 mmol) of the product of Example 14 in 6.0 mL of THF/methanol (1:1) was added 1.9mL of 1.0N sodium hydroxide solution. The reaction was heated to reflux overnight, cooled to room temperature and acidified with 5% HCl solution. The mixture was extracted with ethyl acetate, washed with brine and the combined organics were then dried over $MgSO_4$, filtered and concentrated in vacuo. The residue was triturated with ether/hexanes (1:1) and the solid was collected and dried in vacuo to provide 0.191 g (90%) of the desired carboxylic acid product as a white solid. Electrospray Mass Spec: 543.8 $(M+H)^+$

EXAMPLE 48

2-[(4-But-2-ynyloxy-benzenesulfonyl)-methyl-amino]-5-iodo-3-methyl-benzoic acid

To a solution of 0. 102 g (0.199 mmol) of the product of Example 17 in 6.0 mL of THF/methanol (1:1) was added 1.0 mL of 1.0N sodium hydroxide solution. The reaction was heated to reflux overnight, cooled to room temperature and acidified with 5% HCl solution. The mixture was extracted with ethyl acetate, washed with brine and the combined organics were then dried over $MgSO_4$, filtered and concentrated in vacuo to provide 0.089 g (90%) of the desired carboxylic acid product as a white solid. Electrospray Mass Spec: 499.8 (M+H)+

EXAMPLE 49

2-[Benzyl-(4-but-2-ynyloxy-benzenesulfonyl)-amino]-3,5-dimethyl-benzoic acid

To a solution of 0.161 g (0.338 mmol) of the product of Example 20 in 4.0 mL of THF/methanol (1:1) was added 1.7 mL of 1.0N sodium hydroxide solution. The reaction was heated to reflux overnight, cooled to room temperature and acidified with 5% HCl solution. The mixture was extracted with dichloromethane and the combined organics were then dried over MgSO$_4$, filtered and concentrated in vacuo to provide 0.151 g (97%) of the desired carboxylic acid product as a white solid. Electrospray Mass Spec: 464.0 (M+H)+

EXAMPLE 50

5-Bromo-3-metlhyl-2-{methyl-[4-(4-pyrrolidin-1-yl-but-2-ynyloxy)-benzenesulfonyl]-amino}-benzoic acid To a solution of 0.157 g (0.293 mmol) of the product of Example 23 in 4.0 mL of THF/methanol (1:1) was added 1.5 mL of 1.0N sodium hydroxide solution. The reaction was heated to reflux overnight, cooled to room temperature and brought to pH6–7 with 5% HCl solution. The mixture was extracted with dichloromethane and the combined organics were then dried over Na$_2$SO$_4$, filtered and concentrated in vacuo to provide 0.139 g (91%) of the desired carboxylic acid product as a white solid. Electrospray Mass Spec: 520.9 (M+H)+

EXAMPLE 51

5-Bromo-2-{[4-(4-diethylamino-but-2-ynyloxy)-benzenesulfonyl]-methyl-amino}-3-methyl-benzoic acid According to the procedure of Example 50 0.180 g (0.335 mmol) of the product of Example 24 provides 0.175 g (100%) of the desired carboxylic acid as a tan foam. Electrospray Mass Spec: 522.9 (M+H)+

EXAMPLE 52

5-Bromo-3-methyl-2-[methyl-(4-prop-2-ynyloxy-benzenesulfonyl)-amino]-benzoic acid According to the procedure of Example 38 0.250 g (0.553 mmol) of the product of Example 5 provides 0.237 g (98%) of the desired carboxylic acid as a white solid. Electrospray Mass Spec: 435.8 (M−H)−

EXAMPLE 53

5-Bromo-N-hydroxy-3-methyl-2-[methyl-(4-prop-2-ynyloxy-benzenesulfonyl)-amino]-benzamide According to the procedure of Example 39 0.173 g of the product of Example 52 provides 0.176 g (98%) of the hydroxamic acid as a white solid. Electrospray Mass Spec: 452.8 (M+H)+

EXAMPLE 54

5-Benzofuran-2-yl-2-[(4-methoxy-benzenesulfonyl)-pyridin-3-ylmethyl-amino]-3-methyl-benzoic acid methyl ester According to the procedure of Example 39 0.084 g of the product of Example 6 provides 0.087 g (100%) of the hydroxamic acid as a white foam. Electrospray Mass Spec: 466.8 (M+H)+

EXAMPLE 55

5-Bromo-N-hydroxy-3-methyl-2-[methyl-(4-pent-2-ynyloxy-benzenesulfonyl)-amino]-benzamide According to the procedure of Example 39 0.162 g of the product of Example 7 provides 0.135 g (81%) of the hydroxamic acid as a tan foam. Electrospray Mass Spec: 480.8 (M+H)+Example 56

5-Bromo-2-[(4-hept-2-ynyloxy-benzenesulfonyl)-methyl-amino]-N-hydroxy-3-methyl-benzamide According to the procedure of Example 39 0.180 g of the product of Example 8 provides 0.127 g (69%) of the hydroxamic acid as a tan foam. Electrospray Mass Spec: 508.8 (M+H)+

EXAMPLE 57

5-Bromo-2-[(4-hex-2-ynyloxy-benzenesulfonyl)-methyl-amino]-N-hydroxy-3-methyl-benzamide According to the procedure of Example 39 0.128 g of the product of Example 10 provides 0.087 g (100%) of the hydroxamic acid as a clear glass. Electrospray Mass Spec: 497.0 (M+H)+

EXAMPLE 58

5-Bromo-N-hydroxy-2-{[4-(4-methoxy-but-2-ynyloxy)-benzenesulfonyl]-methyl-amino}-3-methyl-benzamide According to the procedure of Example 39 0.064 g of the product of Example 26 provides 0.062 g (100%) of the hydroxamic acid as a tan foam. Electrospray Mass Spec: 496.8 (M+H)+

EXAMPLE 59

5-Bromo-N-hydroxy-3-methyl-2-{methyl-[4-(3-phenyl-prop-2-ynyloxy)-benzenesulfonyl]-amino}-benzamide According to the procedure of Example 39 0.146 g of the product of Example 44 provides 0.141 g (94%) of the hydroxamic acid as a pale yellow foam. Electrospray Mass Spec: 528.8 (M+H)+

EXAMPLE 60

5-Bromo-N-hydroxy-2-({4-[3-(3-methoxy-phenyl)-prop-2-ynyloxy]-benzenesulfonyl}-methyl-amino)-3-methyl-benzamide According to the procedure of Example 39 0.154 g of the product of Example 45 provides 0.151 g (96%) of the hydroxamic acid as a light orange solid. Electrospray Mass Spec: 558.8 (M+H)+

EXAMPLE 61

5-Bromo-N-hydroxy-2-({4-[3-(2-methoxy-phenyl)-prop-2-ynyloxy]-benzenesulfonyl}-methyl-amino)-3-methyl-benzamide According to the procedure of Example 39 0.135 g of the product of Example 46 provides 0.132 g (95%) of the hydroxamic acid as a white foam. Electrospray Mass Spec: 558.9 (M+H)+

EXAMPLE 62

5-Bromo-N-hydroxy-2-({4-[3-(4-methoxy-phenyl)-prop-2-ynyloxy]-benzenesulfonyl}-methyl-amino)-3-methyl-benzamide According to the procedure of Example 39 0.158 g of the product of Example 47 provides 0.116 g (72%) of the hydroxamic acid as a pale yellow foam. Electrospray Mass Spec: 558.9 (M+H)$^+$

EXAMPLE 63

2-[(4-But-2-ynyloxy-benzenesulfonyl)-methyl-amino]-N-hydroxy-5-iodo-3-methyl-benzamide According to the procedure of Example 39 0.109 g of the product of Example 48 provides 0.112 g (100%) of the hydroxamic acid as a white foam. Electrospray Mass Spec: 514.8 (M+H)$^+$

EXAMPLE 64

2-[Benzyl-(4-but-2-ynyloxy-benzenesulfonyl)-amino]-N-hydroxy-3,5-dimethyl-benzamide According to the procedure of Example 39 0.135 g of the product of Example 49 provides 0.134 g (96%) of the hydroxamic acid as a white solid. Electrospray Mass Spec: 479.0 (M+H)$^+$

EXAMPLE 65

5-Bromo-N-hydroxy-3-methyl-2-{methyl-[4-(4-pyrrolidin-1-yl-but-2-ynyloxy)-benzenesulfonyl]-amino}-benzamide To a 0° solution of 0.33 mL (0.650 mmol) of a 2.0M solution of oxalyl chloride in dichloromethane, diluted with 2.7 mL of dichloromethane, is added 0.050 mL (0.650 mmol) of DMF and the reaction is stirred for 15 minutes at 0°. A solution of 0.113 g (0.217 mmol) of the carboxylic acid product of Example 50, dissolved in 1 mL of DMF, was added to the reaction and the resulting mixture is stirred for 1 h at room temperature and then poured into a 0° mixture of 0.7 mL of water, 3.4 mL of THF and 0.2 mL of a 50% aqueous solution of hydroxylamine. The reaction is allowed to warm to room temperature overnight and the organics are then concentrated in vacuo. The residue is diluted with ethyl acetate, washed with water and saturated sodium bicarbonate, dried over Na$_2$SO$_4$, filtered and concentrated in vacuo to provide 0.087 g (75%) of the hydroxamic acid as a tan foam.

To a solution of 0.065 g (0.121 mmol) of the amino-hydroxamic acid dissolved in 2.0 mL of dichloromethane was added 0.24 mL (0.24 mmol) of a 1.0M solution of HCl in ether. The resulting mixture was stirred for 1 h at room temperature and then diluted with ether. The precipitate was filtered, washed with ether and dried in vacuo to provide 0.064 g (93%) of the hydrochloride salt of the amino-hydroxamic acid as a brown solid. Electrospray Mass Spec: 535.9 (M+H)$^+$

EXAMPLE 66

5-Bromo-2-{[4-(4-diethylaniino-but-2-ynyloxy)-benzenesulfonyl]-methyl-amino}-N-hydroxy-3-methyl-benzamide To a 0° solution of 0.38 mL (0.757 mmol) of a 2.0M solution of oxalyl chloride in dichloromethane, diluted with 3.1 mL of dichloromethane, is added 0.059 mL (0.757 mmol) of DMF and the reaction is stirred for 15 minutes at 0°. A solution of 0.132 g (0.252 mmol) of the carboxylic acid product of Example 51, dissolved in 1 mL of DMF, was added to the reaction and the resulting mixture is stirred for 1 h at room temperature and then poured into a 0° mixture of 0.8 mL of water, 3.9 mL of THF and 0.24 mL of a 50% aqueous solution of hydroxylamine. The reaction is allowed to warm to room temperature overnight and the organics are then concentrated in vacuo. The residue is diluted with ethyl acetate, washed with water and saturated sodium bicarbonate, dried over Na$_2$SO$_4$, filtered and concentrated in vacuo to provide 0.126 g (93%) of the hydroxamic acid as a tan foam.

To a solution of 0.093 g (0.173 mmol) of the amino-hydroxamic acid dissolved in 3.0 mL of dichloromethane was added 0.35 mL (0.35 mmol) of a 1.0M solution of HCl in ether. The resulting mixture was stirred for 1 h at room temperature and then diluted with ether. The precipitate was filtered, washed with ether and dried in vacuo to provide 0.091 g (92%) of the hydrochloride salt of the amino-hydroxamic acid as a tan solid. Electrospray Mass Spec: 540.0 (M+H)$^+$

EXAMPLE 67

5-Bromo-2-[(4-but-2-ynyloxy-benzenesulfonyl)-(4-methyl-piperazin-1-ylmethyl)-amino]-N-hydroxy-3-methyl-benzamide According to the procedure of Example 50 0.128 g (0.228 mmol) of the product of Example 22 provided 0.117 g (94%) of the carboxylic acid. Electrospray Mass Spec: 550.0 (M+H)$^+$ To a 0° solution of 0.27 mL (0.547 mmol) of a 2.0M solution of oxalyl chloride in dichloromethane, diluted with 2.4 mL of dichloromethane, is added 0.042 mL (0.547 mmol) of DMF and the reaction is stirred for 15 minutes at 0°. A solution of 0.100 g (0.182 mmol) of the carboxylic acid, dissolved in 1 mL of DMF, was added to the reaction and the resulting mixture is stirred for 1 h at room temperature and then poured into a 0° mixture of 0.5 mL of water, 2.7 mL of THF and 0.5 mL of a 50% aqueous solution of hydroxylamine. The reaction is allowed to warm to room temperature overnight and the organics are then concentrated in vacuo. The residue is diluted with ethyl acetate, washed with water and saturated sodium bicarbonate, dried over Na$_2$SO$_4$, filtered and concentrated in vacuo to provide 0.080 g (78%) of the hydroxamic acid as a tan foam. Electrospray Mass Spec: 565.1 (M+H)$^+$ To a solution of 0.060 g (0.107 mmol) of the amino-hydroxamic acid dissolved in 4.0 mL of dichloromethane was added 0.43 mL (0.43 mmol) of a 1.0M solution of HCl in ether. The resulting mixture was stirred for 1 h at room temperature and then diluted with ether. The precipitate was filtered, washed with ether and dried in vacuo to provide 0.068 g (100%) of the bis-hydrochloride salt of the piperazinehydroxamic acid as a tan solid. Electrospray Mass Spec: 565.0 (M+H)$^+$

EXAMPLE 68

5-Bromo-3-methyl-2-(methyl-{4-[4-(tetrahydro-pyran-2-yloxy)-but-2-ynyloxy]-benzenesulfonyl}-amino)-benzoic acid According to the procedure of Example 50 0.550 g (0.972 mmol) of the product of Example 15 provided 0.448 g (84%)

of the carboxylic acid as a white solid. Electrospray Mass Spec: 549.9 (M−H)−

EXAMPLE 69

5-Bromo-N-hydroxy-3-methyl-2-(methyl-{4-[4-(tetrahydro-pyran-2-yloxy)-but-2-ynyloxy]-benzenesulfonyl}-amino)-benzamide To a solution of 0.41 g (0.745 mmol) of the product of Example 68 in 4.0 mL of DMF was added 0.121 g (0.893 mmol) of 1-hydroxy benzotriazole (HOBT) followed by 0.190 g (0.990 mmol) of 1-(3-dimethylaminopropyl)-3-ethylcarbodiimide hydrochloride (EDC). The resultin mixture was stirred at room temperature for 1 h and then 0.23 mL of a 50% aqueous solution of hydroxylamine was added and the reaction was stirred overnight. The reaction was then diluted with ethyl acetate and washed with water, 5% HCl solution and saturated sodium bicarbonate solution. The organics were dried over $Na_2SO_4$, filtered and concentrated in vacuo to provide 0.337 g (80%) of the hydroxamic acid as a white foam. Electrospray Mass Spec: 568.8 $(M+H)^+$

EXAMPLE 70

5-Bromo-N-hydroxy-2-{[4-(4-hydro-but-2-ynyloxy)-benzenesulfony]-methyl-amino}-3-methyl-benzamide To a solution of 0.274 g (0.483 mmol) of the product of Example 69 in 4.0 mL of methanol was added 0.012 g (0.048 mmol) of pyridinium p-toluenesulfonate and the resulting mixture was heated to reflux for 18 h. The reaction was then concentrated in vacuo, diluted with ethyl acetate and washed with 5% HCl solution, water and saturated sodium bicarbonate solution. The organics were dried over $Na_2SO_4$, filtered and concentrated in vacuo to provide 0.159 g (68%) of the hydroxamic acid as a white powder. Electrospray Mass Spec: 482.8 $(M+H)^+$

EXAMPLE 71

4-[(4-Hydroxy-benzenesulfonyl)-methyl-amino]-5-methyl-biphenyl-3-carboxylic acid methyl ester To 28 mL of degassed ethylene glycol dimethyl ether was added 2.15 g (5.19 mmol) of the product of Example 4, 0.696 g (5.71 mmol) of phenylboronic acid, 0.300 g (0.26 mmol) of tetrakis(triphenylphosphine)palladium(0), and 10.4 mL (20.8 mmol) of 2M $Na_2CO_3$ and the mixture was refluxed under nitrogen for 18 h. The reaction was then cooled, diluted with ethyl acetate, washed with water and brine, dried over $Na_2SO_4$, filtered and concentrated in vacuo. The residue was triturated with 1:3 dichloromethane/hexanes to provide 1.89 g (89%) of the desired biphenyl product as a pale orange solid. Electrospray Mass Spec 412.4 $(M+H)^+$

EXAMPLE 72

4-{[4-(tert-Butyl-dimethyl-silanyloxy)-benzenesulfonyl]-methyl-amino}-5-methyl-biphenyl-3-carboxylic acid methyl ester A mixture of 1.89 g (4.6 mmol) of the product of Example 71, 0.833 g (5.52 mmol) of t-butyldimethylsilyl chloride and 0.783 g (1.51 mmol) of imidazole in 8 mL of DMF was stirred at room temperature for 18 h. The reaction was quenched with water and extracted with dichloromethane. The organic layer was separated, washed with brine, dried over $Na_2SO_4$ and concentrated in vacuo. The residue was chromatographed on silica gel eluting with ethyl acetate/hexanes (1:20) to provide 1.89 g (78%) of the desired silyl ether product as a white solid. Electrospray Mass Spec 526.0 $(M+H)^+$

EXAMPLE 73

4-[(4-Hydroxy-benzenesulfonyl)-methyl-amino]-5-(4-methyl-piperazin-1-ylmethyl)-biphenyl-3-carboxylic acid methyl ester A mixture of 1.84 g (3.5 mmol) of the product of Example 72 and 0.748 g (4.2 mmol) of N-bromosuccinimide in 35 mL of carbon tetrachloride was refluxed with sun lamp under nitrogen for 2.5 h. The reaction was cooled, washed with water and brine, dried over $Na_2SO_4$ and concentrated in vacuo to give 2.33 g of the benzylic bromide. The bromide was combined with 0.350 g (3.5 mmol) of N-methyl piperazine and 1.45 g (10.5 mmol) of $K_2CO_3$ in 20 mL of DMF and the mixture was stirred at room temperature for 18 h. The reaction mixture was diluted with dichloromethane, washed with water and brine, dried over $Na_2SO_4$ and concentrated in vacuo. The residue was chromatographed on silica gel eluting with 2% methanol/dichloromethane to provide 1.33 g (74%) of the desired product as a pale yellow solid. Electrospray Mass Spec 510.0 $(M+H)^+$

EXAMPLE 74

4-[(4-But-2-ynyloxy-benzenesulfonyl)-methyl-amino]-5-(4-methyl-piperazin-1-yl methyl)-biphenyl-3-carboxylic acid methyl ester To a solution of 0.810 g (1.59 mmol) of the product of Example 73 and 0.594 mL (7.95 mmol) of 2-butyn-1-ol in 8 mL of THF, was added 2.08 g (7.95 mmol) of triphenylphosphine and then 1.25 mL (7.95 mmol) of diethyl azodicarboxylate. The mixture was stirred at room temperature for 18 h, diluted with ethyl acetate, washed with water and brine, dried over $Na_2SO_4$, and concentrated in vacuo. The residue was chromatographed on silica gel with 2% methanol/dichloromethane to provide 0.830 g (93%) of the desired product as a beige solid. Electrospray Mass Spec 562.1 $(M+H)^+$

EXAMPLE 75

4-[(4-But-2-ynyloxy-benzenesulfonyl)-methyl-amino]-5-(4-methyl-piperazin-1-yl methyl)-biphenyl-3-carboxylic acid A mixture of 0.965 g (1.72 mmol) of the product of Example 74 and 8.6 mL (8.59 mmol) of 1N NaOH in 8.6 mL of THF and 8. 6 mL of methanol was heated to reflux for 18 h. The reaction mixture was cooled and neutralized with 3N HCl. The organic solvents were removed and the resulting aqueous solution was extracted with dichloromethane. The organic layer was separated, washed with water and brine, dried over $Na_2CO_3$ and concentrated in vacuo. The residue was triturated with ether to provide 0.829 g (89%) of the desired product as a cream solid. Electrospray Mass Spec 548.1 $(M+H)^+$

EXAMPLE 76

4- [(4-But-2-ynyloxy-benzenesulfonyl)-methyl-amino]-5-(4-methyl-piperazin-1-ylmethyl)-biphenyl-3-carboxylic acid hydroxyamide dihydro-chloride salt To a solution of 0.244 mL (0.487 mmol) of a 2M solution of oxalyl chloride in dichloromethane at 0° C. was added 0.038 mL (0.487 mmol) of DMF and the mixture was stirred for 1 h at room temperature. A solution of 0.089 g (0.163 mmol) of the product of Example 75 in 0.5 mL dichloromethane was then added to the reaction mixture and the resulting mixture was stirred for 1 h at room temperature.

In a separate flask, a mixture of 0.149 mL (2.44 mmol) of 50% aqueous hydroxylamine in 2.5 mL THF and 0.5 mL water was cooled for 15 min at 0° C. and the acid chloride solution was added to it in one portion. The resulting solution was allowed to warm to room temperature with stirring overnight. The reaction mixture was diluted with dichloromethane and washed with water and brine, dried over $NA_2SO_4$, filtered and concentrated in vacuo. The residue was triturated with ether to provide 0.066 g (72%) of the desired hydroxamic acid as a beige solid.

To a solution of 0.240 g (0.418 mmol) of the hydroxamic acid in 5 mL dichloromethane, was added 1.67 mL (1.67 mmol) of 1M HCl/ether solution. The reaction was stirred for 1 h and then diluted with ether. The resulting precipitate was filtered and dried in vacuo to provide 0.245 g (92%) of the desired hydrochloride salt as a beige solid. Electrospray Mass Spec 563.1 $(M+H)^+$

EXAMPLE 77

5-Bromo-3-methyl-2-{methyl-[4-(1-methyl-prop-2-ynyloxy)-benzenesulfonyl]-amino}-benzoic acid methyl ester According to the procedure of Example 5, 0.400 g (0.966 mmol) of the product of Example 4 and 0.083 mL (1.063 mmol) of 3-butyn-2-ol provided 0.266 g (59%) of the propargylic ether as a colorless oil. Electrospray Mass Spec 465.8 $(M+H)^+$

EXAMPLE 78

5-Bromo-3-methyl-2-{methyl-[4-(1-methyl-prop-2-ynyloxy)-benzenesulfonyl]-amino}-benzoic acid According to the procedure of Example 10, 0.241 g of the product of Example 77 was hydrolyzed with 2.6 mL of 1.0N sodium hydroxide solution to provide 0.073 g (31%) of the desired carboxylic acid as a white solid and 0.034 g (14%) of the starting ester. Electrospray Mass Spec 451.8 $(M+H)^+$

EXAMPLE 79

5-Bromo-N-hydroxy-3-methyl-2-{methyl-[4-(1-methyl-prop-2-ynyloxy)-benzenesulfonyl]-amino}-benzamide According to the procedure of Example 39, 0.068 g (0.150 mmol) of the product of Example 34 provided 0.070 g (100%) of the hydroxamic acid as a white foam. Electrospray Mass Spec 466.9 $(M+H)^+$

EXAMPLE 80

3-[3-(tert-Butyl-dimethyl-silanyloxy)-phenyl]-prop-2-yn-1-ol

To a solution of 2.0 g (9.091 mmol) of 3-iodophenol in 10 mL of DMF was added 1.55 g (0.023 mol) of imidazole and 1.64 g (0.011 mol) of t-butyldimethylsilyl chloride and the resulting mixture was stirred at room temperature for 48 h. The reaction was then diluted with ether and washed with water, dried over $Na_2SO_4$, filtered and concentrated in vacuo. The residue was used in the next step without purification.

To a solution of 3.04 g (9.091 mmol) of the silylated iodoaryl in 55 mL of diethylamine was added 0.53 mL of propargyl alcohol followed by 0.173 g (0.909 mmol) of copper (I) iodide and 0.32 g (0.456 mmol) of bis(triphenylphosphine)palladium(II)dichloride. The resulting mixture was stirred for 4 h at room temperature and then concentrated in vacuo. The residue was chromatographed on silica gel eluting with ethyl acetate/hexanes (1:10) to provide 0.73 g (31%) of the aryl acetylene as a brown oil. EI Mass Spec 262 $(M^+)$

EXAMPLE 81

5-Bromo-2-({4-[3-(3-hydroxy-phenyl)-prop-2-ynyloxy]-benzenesulfonyl}-methyl-amino)-3-methyl-benzoic acid According to the procedure of Example 5, 0.158 g (0.604 mmol) of the product of Example 80 and 0.250 g (0.604 mmol) of the product of Example 4 provided 0.315 g of the propargylic ether.

According to the procedure of Example 10, 0.315 g of the propargylic ether provided 0.169 g (67%) of the phenol-carboxylic acid as a tan solid. Electrospray Mass Spec 527.9 $(M-H)^-$

EXAMPLE 82

5-Bromo-2-[(4-{3-[3-(tert-butyl-dimethyl-silanyloxy)-phenyl]-prop-2-ynyloxy}-benzenesulfonyl)-methyl-amino]-3-methyl-benzoic acid To a solution of 0.144 g (0.271 mmol) of the product of Example 81 in 1.0 mL of DMF was added 0.092 g (1.356 mmol) of imidazole and 0.098 g (0.651 mmol) of t-butyldimethylsilyl chloride and the mixture was stirred at room temperature for 15 h. The reaction mixture was then poured into 20 mL of water and stirred for 5 h and then extracted with ether. The organics were washed with water, dried over $NA_2SO_4$, filtered and concentrated in vacuo. The residue was chromatographed on silica gel eluting with ethyl acetate/hexanes (1:3) to provide 0.136 g of the carboxylic acidsilylated phenol as a white solid. Electrospray Mass Spec 643.8 $(M+H)^+$

EXAMPLE 83

5-Bromo-2-[(4-{3-[3-(tert-butyl-dimethyl-silanyloxy)-phenyl]-prop-2-ynyloxy}-benzenesulfonyl)-methyl-amino]-N-hydroxy-3-methyl-benzamide According to the procedure of Example 39, 0.097 g (0.150 mmol) of the product of Example 82 provided 0.099 g of the hydroxamic acid as a white solid. Electrospray Mass Spec 658.9 $(M+H)^+$

EXAMPLE 84

5-Bromo-N-hydroxy-2-({4-[3-(3-hydroxy-phenyl)-prop-2-ynyloxy]-benzenesulfonyl}-methyl-amino)-3-methyl-benzamide To a solution of 0.099 g (0.150 mmol) of the product of Example 83 in 1 mL of acetonitrile was added 3 mL of a 5% solution of 48% HF in acetonitrile and the resulting solution was stirred at room temperature for 15 h. The reaction mixture was then diluted with water and ethyl acetate. The organic layer was washed with water, dried over $Na_2SO_4$ and concentrated in vacuo to give 0.031 g (38%) of the phenol hydroxamic acid as a pale yellow solid. Electrospray Mass Spec 544.9 (M+H)+

EXAMPLE 85

4-But-2-ynyloxy-benzenesulfonic acid sodium salt

To a solution of 52.35 g (0.225 mol) of 4-hydroxybenzenesulfonate sodium salt in 1L of isopropanol and 225 mL of a 1.0N solution of sodium hydroxide was added 59.96 g (0.45 mol) of 1-bromo-2-butyne. The resulting mixture was heated to 70° for 15 h and then the isopropanol was removed by evaporation in vacuo. The resulting white precipitate was collected by filtration, washed with isopropanol and ether and dried in vacuo to give 56.0 g (100%) of the butynyl ether as a white solid.

EXAMPLE 86

4-But-2-ynyloxy-benzenesulfonyl chloride

To a 0° solution of 43.8 mL (0.087 mol) of 2M oxalyl chloride/dichloromethane solution in 29 mL of dichloromethane was dropwise added 6.77 mL (0.087 mol) of DMF followed by 7.24 g (0.029 mol) of the product of Example 85. The reaction mixture was stirred for 10 minutes at 0° then let warm to room temperature and stirred for 2 days. The reaction was then poured into ice and extracted with 150 mL of hexanes. The organics were washed with water and brine, dried over $Na_2SO_4$, filtered and concentrated in vacuo to provide 6.23 g (88%) of the sulfonyl chloride as a yellow solid; m.p. 63–65° C. EI Mass Spec: 243.9 MH+

EXAMPLE 87

But-2-ynyloxy-benzene

According to the procedure of Example 5, 2.00 g (0.021 mol) of phenol and 1.64 g (0.023 mol) of 2-butyn-1-ol provided 2.18 g (70%) of the butynyl ether as a clear liquid. EI Mass Spec: 146.0 MH+

EXAMPLE 88

4-But-2-ynyloxy-benzenesulfonyl chloride

To a solution of 0.146 g (1.0 mmol) of the product of Example 87 in 0.3 mL of dichloromethanein an acetone/ice bath under $N_2$ was dropwise added a solution of 0.073 mL (1.1 mmol) of chlorosulfonic acid in 0.3 mL of dichloromethane. After the addition was complete, the ice bath was removed and the reaction was stirred at room temperature for 2 h. To the reaction was then dropwise added 0.113 mL (1.3 mmol) of oxalyl chloride, followed by 0.015 mL DMF. The reaction was heated to reflux for 2 h and then diluted with hexane and poured into ice water. The organic layer was washed with brine, dried over sodium sulfate, and concentrated in vacuo to provide 0.130 mg (53%) of the desired product as a light brown solid.

Pharmacology

Representative compounds of this invention were evaluated as inhibitors of the enzymes MMP-1, MMP-9, MMP-13 and TNF-α converting enzyme (TACE). The standard pharmacological test procedures used, and results obtained which establish this biological profile are shown below.

Test Procedures for Measuring MMP-1, MMP-9, and MMP-13 Inhibition

These standard pharmacological test procedures are based on the cleavage of a thiopeptide substrates such as Ac-Pro-Leu-Gly(2-mercapto-4-methyl-pentanoyl)-Leu-Gly-OEt by the matrix metalloproteinases MMP-1, MMP-13 (collagenases) or MMP-9 (gelatinase), which results in the release of a substrate product that reacts colorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM $CaCl_2$) before use. The stock of enzyme is diluted with buffer (50 mM HEPES, pH 7.5, 5 mM $CaCl_2$, 0.02% Brij) to the desired final concentration. The buffer, enzyme, vehicle or inhibitor, and DTNB/substrate are added in this order to a 96 well plate (total reaction volume of 200 μl) and the increase in color is monitored spectrophotometrically for 5 minutes at 405 nm on a plate reader and the increase in color over time is plotted as a linear line.

Alternatively, a fluorescent peptide substrate is used. In this test procedure, the peptide substrate contains a fluorescent group and a quenching group. Upon cleavage of the substrate by an MMP, the fluorescence that is generated is quantitated on the fluorescence plate reader. The assay is run in HCBC assay buffer (50 mM HEPES, pH 7.0, 5 mM $Ca^{+2}$, 0.02% Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide test procedures, the slope of the line is calculated and represents the reaction rate. The linearity of the reaction rate is confirmed ($r^2>0.85$). The mean (x±sem) of the control rate is calculated and compared for statistical significance (p<0.05) with drug-treated rates using Dunnett's multiple comparison test. Dose-response relationships can be generated using multiple doses of drug and $IC_{50}$ values with 95% CI are estimated using linear regression.

Test Procedure for Measuring TACE Inhibition

Using 96-well black microtiter plates, each well receives a solution composed of 10 μL TACE (final concentration 1 μg/mL), 70 μL Tris buffer, pH 7.4 containing 10% glycerol (final concentration 10 mM), and 10 μL of test compound solution in DMSO (final concentration 1 μM, DMSO concentration <1%) and incubated for 10 minutes at room temperature. The reaction is initiated by addition of a fluorescent peptidyl substrate (final concentration 100 μM) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2>0.85$). The mean (x±sem) of the control rate is calculated and compared for statistical significance (p<0.05) with drug-treated rates using Dunnett's multiple comparison test. Dose-response relationships can be generate using multiple doses of drug and $IC_{50}$ values with 95% CI are estimated using linear regression.

Human Monocvtic THP-1 Cell Differentiation Assay For Soluble Proteins (THP-1 Soluble Protein Assay)

Mitogenic stimulation of THP-1 cells cause differentiation into macrophage like cells with concomitant secretion of tumor necrosis factor (TNF-a) and TNF receptor (TNF-R p75/80 and TNF-R p55/60) and Interleukin-8 (IL-8), among other proteins. In addition, non-stimulated THP-1 cells shed both the p75/80 and the p55/60 receptors over time. The release of membrane bound TNF-α and possibly TNF-R p75/80 and TNF-R p55/60, but not IL-8, is mediated by an enzyme called TNF-a converting enzyme or TACE. This assay can be used to demonstrate either an inhibitory or a stimulatory compound effect on this TACE enzyme and any cytotoxic consequence of such a compound.

THP-1 cells (from ATCC) are a human monocytic cell line which were obtained from the peripheral blood of a one year old male with acute monocytic leukemia. They can be grown in culture and differentiated into macrophage like cells by stimulation with mitogens.

For the assay, THP-1 cells are seeded from an ATCC stock which was previously grown and frozen back at 5×106/ml/vial. One vial is seeded into a T25-flask with 16 mls of RPMI-1640 with glutamax (Gibco) media containing 10 % fetal bovine serum, 100 units/ml penicillin, 100 μg/ml streptomycin, and $5 \times 10^{-5}$ M 2-mercapto-ethanol (THP-1 media). Each vial of cells are cultured for about two weeks prior to being used for an assay and then are used for only 4 to 6 weeks to screen compounds. Cells are subcultured on Mondays and Thursdays to a concentration of 1×105/ml.

To perform an assay, the THP-1 cells are co-incubated in a 24 well plate with 50 ml/well of a 24 mg/ml stock of Lipopolysacharide (LPS) (Calbiochem Lot# B13189) at 37° C. in 5% $CO_2$ at a concentration of $1.091 \times 10^6$ cells/ml (1.1 ml/well) for a total of 24 hours. At the same time, 50 ml/well of drug, vehicle or THP-1 media is plated in appropriate wells to give a final volume of 1.2 ml/well. Standard and test compounds are dissolved in DMSO at a concentration of 36 mM and diluted from here to the appropriate concentrations in THP-1 media and added to the wells at the beginning of the incubation period to give final concentrations of 100 mM, 30 mM, 10 mM, 3 mM, 1 mM, 300 nM, and 100 nM. Cell exposure to DMSO was limited to 0.1 % final concentration. Positive control wells were included in the experiment which had mitogen added but no drug. Vehicle control wells were included as well, which were identical to the positive control wells, except that DMSO was added to give a final concentration of 0.083%. Negative control wells were included in the experiment which had vehicle but no mitogen or drug added to the cells. Compounds can be evaluated for their effect on basal (non-stimulated) shedding of the receptors by replacing the LPS with 50 ml/well of THP-1 media. Plates are placed into an incubator set at 5% CO2 and at 37° C. After 4 hours of incubation, 300 ml/well of tissue culture supernatant (TCS) is removed for use in an TNF-a ELISA. Following 24 hours of incubation, 700 ml/well of TCS is removed and used for analysis in TNF-R p75/80, TNF-R p55/60 and IL-8 ELISAs.

In addition, at the 24 hours timepoint, and the cells for each treatment group are collected by resuspension in 500 μl/well of THP-1 media and transferred into a FACS tube. Two ml/tube of a 0.5 mg/ml stock of propidium iodide (PI) (Boerhinger Mannheim cat. # 1348639) is added. The samples are run on a Becton Dickinson FaxCaliber FLOW cytometry machine and the amount of dye taken up by each cell is measured in the high red wavelength (FL3). Only cells with compromised membranes (dead or dying) can take up PI. The percent of live cells is calculated by the number of cells not stained with PI, divided by the total number of cells in the sample. The viability values calculated for the drug treated groups were compared to the viability value calculated for the vehicle treated mitogen stimulated group ("vehicle positive control") to determine the "percent change from control". This "percent change from control" value is an indicator of drug toxicity.

The quantity of soluble TNF-a, TNF-R p75/80 and TNF-R p55/60 and IL-8 in the TCS of the THP-1 cell cultures are obtained with commercially available ELISAs from R&D Systems, by extrapolation from a standard curve generated with kit standards. The number of cells that either take up or exclude PI are measured by the FLOW cytometry machine and visualized by histograms using commercially available Cytologic software for each treatment group including all controls.

Biological variability in the magnitude of the response of THP-1 cell cultures requires that experiments be compared on the basis of percent change from "vehicle positive control" for each drug concentration. Percent change in each soluble protein evaluated from the "vehicle positive control" was calculated for each compound concentration with the following formula:

$$\% \text{ Change} = \frac{\text{pg/ml (compound)} - \text{pg/ml(veh pos control)}}{\text{pg/ml (veh pos control)} - \text{pg/ml (veh neg control)}} \times 100$$

For the soluble protein (TNF-a, p75/80, p55/60, IL-8) studies under stimulated conditions, the mean pg/ml of duplicate wells were determined and the results expressed as percent change from "vehicle positive control". For the soluble protein (p75/80 and p55/60 receptors) studies under non-stimulated conditions, the mean pg/ml of duplicate wells were determined and the results expressed as percent change from "vehicle positive control" utilizing the following formula:

$$\% \text{ Change} = \frac{\text{pg/ml (compound neg control)} - \text{pg/ml (veh neg control)}}{\text{pg/ml (veh neg control)}} \times 100$$

IC50 values for each compound are calculated by non-linear regression analysis using customized software utilizing the JUMP statistical package.

For the cell viability studies, the viabilities (PI exclusion) of pooled duplicate wells were determined and the results expressed as % change from "vehicle positive control". The viability values calculated for the compound treated groups were compared to the viability value calculated for the "vehicle positive control" to determine "percent change from control" as below. This value "percent change from control" is an indicator of drug toxicity.

$$\% \text{ Change} = \frac{\% \text{ live cells (compound)}}{\% \text{ live cells (veh pos control)}} - 1 \times 100$$

References

Bjomberg, F., Lantz, M., Olsson, I., and Gullberg, U. Mechanisms involved in the processing of the p55 and the p75 tumor necrosis factor (TNF) receptors to soluble receptor forms. Lymphokine Cytokine Res. 13:203–211, 1994.

Gatanaga, T., Hwang, C., Gatanaga, M., Cappuccini, F., Yamamoto, R., and Granger, G. The regulation of TNF mRNA synthesis, membrane expression, and release by PMA- and LPS-stimulated human monocytic THP-1 cells in vitro. Cellular Immun. 138:1–10, 1991.

Tsuchiya, S., Yamabe, M., Yamagughi, Y., Kobayashi, Y., Konno, T., and Tada, K. Establishment and characterization of a human acute monocytic leukemia cell line (THP-1). Int. J. Cancer. 26:1711–176, 1980.

Results of the above in-vitro matrix metalloproteinase inhibition, TACE inhibition and THP standard pharmacological test procedures are given in Table I below.

Table I. Inhibition in MMP, TACE and THP assays:

TABLE 1

|  | $IC_{50}$ (nM) or % Inhibition ($\mu$M) | | | | % Inhib. @ 3 $\mu$M |
| --- | --- | --- | --- | --- | --- |
| Example # | MMP-1 | MMP-9 | MMP-13 | TACE | THP |
| 31 | 19% (10) | 301 | 724 | 44 | 6 |
| 32 | 26% (10) | 643 | 255 | 58 | 15 |
| 33 | 32% (10) | 1205 | 908 | 29 | 14 |
| 34 | 39% (10) | 790 | 383 | 127 | 22 |
| 36 | 114 | 11 | 21 | 32 | 14 |
| 39 | 2488 | 21 | 68 | 67 | 0 |
| 43 | 4243 | 578 | 518 | 135 | 76 |
| 53 | 113 | 15 | 52 | 11 | 55 |
| 54 | 1616 | 304 | 154 | 16 | 84 |
| 55 | 1228 | 800 | 289 | 12 | 48 |
| 56 | 53% (10) | 389 | 701 | 34 | 16 |
| 57 | 2364 | 232 | 358 | 47 | 11 |
| 58 | 7803 | 387 | 233 | 11 | 46 |
| 59 | 3815 | 857 | 321 | 66 | 20 |
| 60 | 1029 | 671 | 935 | 91 | 1 |
| 61 | 52% (10) | 1507 | 1199 | 193 | 0 |
| 62 | 3602 | 901 | 588 | 104 | 15 |
| 63 | 901 | 840 | 275 | 16 | 87 |
| 64 | 1187 | 830 | 312 | 105 | 48 |
| 65 | 3352 | 602 | 537 | 148 | 12 |
| 66 | 21% (10) | 2827 | 2377 | 346 | 5 |
| 67 | 1658 | 166 | 252 | 25 | 94 |
| 69 | 25% (10) | 396 | 177 | 30 | 19 |
| 70 | 3203 | 477 | 83 | 6.8 | 88 |
| 76 | 1923 | 28 | 47 | 42 | 95 |
| 79 | 1534 | 455 | 433 | 122 | 9 |
| 84 | 113 | 694 | 189 | 34 | 0 |

Based on the results obtained in the standard pharmacological test procedures described above, the compounds of this invention were shown to be inhibitors of the enzymes MMP-1, MMP-9, MMP-13 and TNF-a converting enzyme (TACE) and are therefore useful in the treatment of disorders such as arthritis, tumor metastasis, tissue ulceration, abnormal wound healing, periodontal disease, graft rejection, insulin resistance, bone disease and HIV infection.

The compounds of this invention are also useful in treating or inhibiting pathological changes mediated by matrix metalloproteinases such as atherosclerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, infammatory bowel disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a MMP or TACE dependent condition must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed is:

1. Hydroxamic acids having the formula:

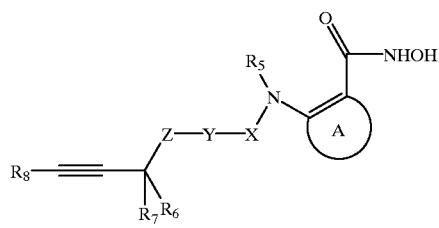

where the C(=O)NHOH moiety and the —$NR_5$— moiety are bonded to adjacent carbons of group A;

wherein A is phenyl, naphthyl, or phenyl fused to a 5 to 7 membered saturated or unsaturated cycloalkyl ring;

X is $SO_2$ or —$P(O)R_{10}$;

Y is phenyl, or naphthyl with the proviso that X and Z may not be bonded to adjacent atoms of Y;

Z is O, NH, CH, or S;

$R_5$ is hydrogen or alkyl of 1–6 carbon atoms;

$R_6$ and $R_7$ are each, independently, hydrogen, alkyl of 1–6 carbon atoms, —CN, —CCH;

and $R_8$ is hydrogen, alkyl of 1–6 carbon atoms, alkenyl of 2–6 carbon atoms, alkynyl of 2–6 carbon atoms, cycloalkyl of 3–6 carbon atoms, phenyl, or naphthyl;

$R_9$ is hydrogen, phenyl, naphthyl, alkyl of 1–6 carbon atoms, or cycloalkyl of 3–6 carbon atoms;

and $R_{10}$ is phenyl, naphthyl, alkyl of 1–6 carbon atoms, or cycloalkyl of 3–6 carbon atoms,;

or a pharmaceutically acceptable salt thereof.

2. A compound of claim 1 wherein the ring atom of A adjacent to the the —$NR^5$— is carbon and has a substituent other than hydrogen.

3. A compound of claim 1 wherein both of the carbons of A adjacent to the —$NR^5$— has a substituent other than hydrogen, and the carbon of group A para to the —$NR^5$— group has a substituent other than hydrogen.

4. A compound of claim 1 in which A is a phenyl wherein both of the carbons of A adjacent to the —$NR^5$— group has a substituent other than hydrogen, and the carbon of group A para to the —$NR^5$— group has a substituent other than hydrogen.

5. A compound according to claim 4 wherein Y is a phenyl ring substituted at the 1- and 4-positions by X and Z, respectively.

6. A compound according to claim 5 wherein X is $SO_2$.

7. A compound according to claim 5 wherein X is $SO_2$ and Z is oxygen.

8. A compound according to claim 5 wherein X is $SO_2$, Z is oxygen, and $R_6$ and $R_7$ are hydrogen.

9. A compound according to claim 5 wherein X is $SO_2$, Z is oxygen, $R_6$ and $R_7$ are hydrogen, and $R_8$ is —$CH_2OH$ or methyl.

10. A compound according to claim 1 which is selected from the group consisting of:

5-Bromo-2-{[4-(4-cyclobutylamino-but-2-ynyloxy)-benzenesulfonyl]-methyl-amino}-N-hydroxy-3-methyl-benzamide;

5-Bromo-N-hydroxy-3-methyl-2-{methyl-[4-(4-methylamino-but-2-ynyloxy)-benzenesulfonyl]-amino}-benzamide;

5-Bromo-2-({4-[4–3-dimethylamino-propylamino)-but-2-ynyloxy]-benzenesulfonyl}-methyl-amino)-N-hydroxy-3-methyl-benzamide;

5-Bromo-2-({4-[4-(2-dimethylamino-ethylamino)-but-2-ynyloxy]-benzenesulfonyl}-methyl-amino)-N-hydroxy-3-methyl-benzamide;

4-[(4-But-2-ynyloxy-benzenesulfonyl)-methyl-amino]-5-methyl-biphenyl-3-carboxylic acid hydroxyamide;

5-Bromo-N-hydroxy-3-methyl-2-[methyl-(4-prop-2-ynyloxy-benzenesulfonyl)-amino]-benzamide;

5-Bromo-N-hydroxy-3-methyl-2-[methyl-(4-pent-2-ynyloxy-benzenesulfonyl)-amino]-benzamide;

5-Bromo-2-[(4-hept-2-ynyloxy-benzenesulfonyl)-methyl-amino]-N-hydroxy-3-methyl-benzamide;

5-Bromo-2-[(4-hex-2-ynyloxy-benzenesulfonyl)-methyl-amino]-N-hydroxy-3-methyl-benzamide;

5-Bromo-N-hydroxy-2-{[4-(4-methoxy-but-2-ynyloxy)-benzenesulfonyl]-methyl-amino}-3-methyl-benzamide;

5-Bromo-N-hydroxy-3-methyl-2-{methyl-[4-(3-phenyl-prop-2-ynyloxy)-benzenesulfonyl]-amino}-benzamide;

5-Bromo-N-hydroxy-2-({4-[3-(3-methoxy-phenyl)-prop-2-ynyloxy]-benzenesulfonyl}-methyl-amino)-3-methyl-benzamide;

5-Bromo-N-hydroxy-2-({4-[3-(2-methoxy-phenyl)-prop-2-ynyloxy]-benzenesulfonyl}-methyl-amino)-3-methyl-benzamide;

5-Bromo-N-hydroxy-2-({4-[3-(4-methoxy-phenyl)-prop-2-ynyloxy]-benzenesulfonyl}-methyl-amino)-3-methyl-benzamide;

2-[(4-But-2-ynyloxy-benzenesulfonyl)-methyl-amino]-N-hydroxy-5-iodo-3-methyl-benzamide;

2-[Benzyl-(4-but-2-ynyloxy-benzenesulfonyl)-amino]-N-hydroxy-3,5-diemthyl-benzamide;

5-Bromo-2-{[4-(4-diethylamino-but-2-ynyloxy)-benzenesulfonyl]-methyl-amino}-N-hydroxy-3-methyl-benzamide; or 5-Bromo-N-hydroxy-2-{[4-(4-hydroxy-but-2-ynyloxy)-benzenesulfonyl]-methyl-amino}-3-methyl-benzamide;

or pharmaceutically acceptable salts thereof.

11. A pharmaceutical composition comprising a compound having the formula

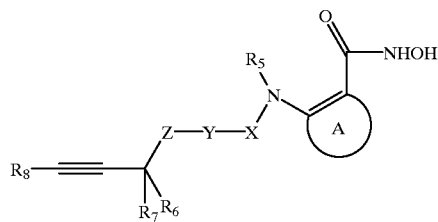

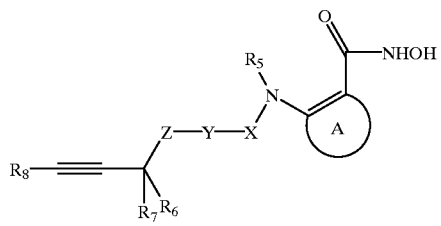

where the C(=O)NHOH moiety and the —NR$_5$— moiety are bonded to adjacent carbons of group A;

wherein A is phenyl, naphthyl, or phenyl fused to a 5 to 7 membered saturated or unsaturated cycloalkyl ring;

X is SO$_2$ or —P(O)R$_{10}$;

Y is phenyl, or naphthyl with the proviso that X and Z may not be bonded to adjacent atoms of Y;

Z is O, NH, CH$_2$ or S;

R$_5$ is hydrogen or alkyl of 1–6 carbon atoms;

R$_6$ and R$_7$ are each, independently, hydrogen, alkyl of 1–6 carbon atoms, —CN, —CCH;

and R$_8$ is hydrogen, alkyl of 1–6 carbon atoms, alkenyl of 2–6 carbon atoms, alkynyl of 2–6 carbon atoms, cycloalkyl of 3–6 carbon atoms, phenyl, or naphthyl;

R$_9$ is hydrogen, phenyl, naphthyl, alkyl of 1–6 carbon atoms, or cycloalkyl of 3–6 carbon atoms;

and R$_{10}$ is phenyl, naphthyl, alkyl of 1–6 carbon atoms, or cycloalkyl of 3–6 carbon atoms;

or a pharmaceutically acceptable salt thereof.

12. A method of inhibiting pathological changes mediated by TNF-α converting enzyme (TACE) in a mammal in need thereof which comprises providing to said mammal a therapeutically effective amount of a compound having the formula where the C(=O)NHOH moiety and the —NR$_5$— moiety are bonded to adjacent carbons of group A;

wherein A is phenyl, naphthyl, or phenyl fused to a 5 to 7 membered saturated or unsaturated cycloalkyl ring;

X is SO$_2$ or —P(O)R$_{10}$;

Y is phenyl, or naphthyl with the proviso that X and Z may not be bonded to adjacent atoms of Y;

Z is O, NH, CH$_2$ or S;

R$_5$ is hydrogen or alkyl of 1–6 carbon atoms;

R$_6$ and R$_7$ are each, independently, hydrogen, alkyl of 1–6 carbon atoms, —CN, —CCH;

and R$_8$ is hydrogen, alkyl of 1–6 carbon atoms, alkenyl of 2–6 carbon atoms, alkynyl of 2–6 carbon atoms, cycloalkyl of 3–6 carbon atoms, phenyl, or naphthyl;

R$_9$ is hydrogen, phenyl, naphthyl, alkyl of 1–6 carbon atoms, or cycloalkyl of 3–6 carbon atoms;

and R$_{10}$ is phenyl, naphthyl, alkyl of 1–6 carbon atoms, or cycloalkyl of 3–6 carbon atoms;

or a pharmaceutically acceptable salt thereof.

13. The method according to claim 12 wherein the condition treated is rheumatoid arthritis, graft rejection, cachexia, inflammation, fever, insulin resistance, septic shock, congestive heart failure, inflammatory disease of the central nervous system, inflammatory bowel disease or HIV infection.

* * * * *